(12) United States Patent
Nishio et al.

(10) Patent No.: US 10,765,838 B2
(45) Date of Patent: Sep. 8, 2020

(54) MEDICAL DEVICE, MEDICAL DEVICE ASSEMBLY, BALLOON DEVICE, AND TREATMENT METHOD FOR TREATING URETHRAL STRICTURE

(71) Applicant: TERUMO KABUSHIKI KAISHA, Shibuya-ku, Tokyo (JP)

(72) Inventors: Kosuke Nishio, Tokyo (JP); Riyaheh S. Hazama, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 683 days.

(21) Appl. No.: 15/053,150

(22) Filed: Feb. 25, 2016

(65) Prior Publication Data

US 2016/0243341 A1  Aug. 25, 2016

(30) Foreign Application Priority Data

Feb. 25, 2015 (JP) .................................. 2015-035833

(51) Int. Cl.
*A61M 25/10* (2013.01)
*A61B 17/34* (2006.01)
(Continued)

(52) U.S. Cl.
CPC ..... *A61M 25/1011* (2013.01); *A61B 17/0469* (2013.01); *A61B 17/062* (2013.01); *A61B 17/3478* (2013.01); *A61F 2/958* (2013.01); *A61B 17/0487* (2013.01); *A61B 2017/00274* (2013.01); *A61B 2017/0409* (2013.01); *A61B 2017/0417* (2013.01); *A61B 2017/0464* (2013.01); *A61B 2017/22044* (2013.01); *A61B 2017/22047* (2013.01); *A61F 2/92* (2013.01); (Continued)

(58) Field of Classification Search
CPC .. A61F 2/958; A61F 2/0089; A61F 2002/047; A61B 2017/00473
See application file for complete search history.

(56) References Cited

U.S. PATENT DOCUMENTS 4,872,874 A * 10/1989 Taheri .................. A61B 17/115
128/898
5,707,385 A * 1/1998 Williams .................. A61F 2/92
604/104
(Continued)

FOREIGN PATENT DOCUMENTS

JP       10-506038 A      6/1998
WO    WO 96/27406 A1    9/1996

*Primary Examiner* — Alexander J Orkin
(74) *Attorney, Agent, or Firm* — Buchanan Ingersoll & Rooney PC

(57) ABSTRACT

A medical device is disclosed for delivering a medical member which is intended to indwell in a treatment site of a urethra includes a flexible main body that extends in an axial direction, a balloon that includes an effectively dilatable portion on which the medical member is mounted, that has a dilating space into which a pressurizing medium flows between an outer surface of the main body and the balloon, and that is capable of dilating deformation and deflating deformation, an elongated guide member that is arranged across the treatment site and the outside of a living body via the urethra, and an attachment portion to which at least a portion of the guide member is detachably attached at a position between both end portions in the axial direction of the main body.

16 Claims, 17 Drawing Sheets

(51) Int. Cl.
  *A61F 2/958* (2013.01)
  *A61B 17/04* (2006.01)
  *A61B 17/062* (2006.01)
  *A61F 2/92* (2013.01)
  *A61B 17/00* (2006.01)
  *A61F 2/04* (2013.01)
  *A61M 25/04* (2006.01)
  *A61B 17/22* (2006.01)

(52) U.S. Cl.
  CPC ........ *A61F 2002/047* (2013.01); *A61M 25/04* (2013.01)

(56) References Cited

U.S. PATENT DOCUMENTS

| | | | | |
|---|---|---|---|---|
| 5,824,052 A * | 10/1998 | Khosravi | ................... | A61F 2/88 623/1.15 |
| 5,833,707 A * | 11/1998 | McIntyre | ................... | A61F 2/92 606/198 |
| 5,984,955 A * | 11/1999 | Wisselink | ................... | A61F 2/07 623/1.35 |
| 6,096,073 A * | 8/2000 | Webster | ................... | A61F 2/91 623/1.16 |
| 6,221,090 B1 * | 4/2001 | Wilson | ................... | A61F 2/856 606/194 |
| 6,231,597 B1 * | 5/2001 | Deem | ................ | A61B 17/12022 606/108 |
| 6,261,304 B1 * | 7/2001 | Hall | ...................... | A61F 2/2493 604/264 |
| 6,413,273 B1 * | 7/2002 | Baum | ...................... | A61F 2/88 606/198 |
| 6,494,905 B1 * | 12/2002 | Zedler | ..................... | A61F 2/958 623/1.11 |
| 7,879,050 B2 * | 2/2011 | Wilk | ................... | A61B 17/122 606/148 |
| 2002/0072763 A1 * | 6/2002 | Chien | ............ | A61B 17/12022 606/194 |
| 2003/0055483 A1 * | 3/2003 | Gumm | .................. | A61F 2/856 623/1.11 |
| 2003/0097169 A1 * | 5/2003 | Brucker | .................. | A61F 2/856 623/1.11 |
| 2003/0171801 A1 * | 9/2003 | Bates | ....................... | A61F 2/07 623/1.13 |
| 2004/0010307 A1 * | 1/2004 | Grad | ....................... | A61F 2/01 623/1.15 |
| 2007/0016241 A1 * | 1/2007 | von Oepen | ............. | A61F 2/958 606/192 |
| 2008/0195041 A1 * | 8/2008 | Goldfarb | ................ | A61M 29/02 604/96.01 |
| 2010/0179648 A1 * | 7/2010 | Richter | ................. | A61F 2/2412 623/2.11 |
| 2014/0018732 A1 * | 1/2014 | Bagaoisan | ........ | A61M 25/0136 604/95.04 |

\* cited by examiner

MEDICAL DEVICE, MEDICAL DEVICE ASSEMBLY, BALLOON DEVICE, AND TREATMENT METHOD FOR TREATING URETHRAL STRICTURE

CROSS-REFERENCES TO RELATED APPLICATIONS

This application claims priority to Japanese Application No. 2015-035833 filed on Feb. 25, 2015, the entire content of which is incorporated herein by reference.

TECHNICAL FIELD

The present disclosure generally relates to a medical device used in delivering a medical member, a medical device assembly including the medical device, a balloon device, and a treatment method for treating a urethral stricture.

BACKGROUND DISCUSSION

In the medical field, in order to treat or rehabilitate a patient who suffers from certain diseases, manual skills are used in the related art, in which various medical members delivered into a biological lumen (for example, a lumen in a living body such as a blood vessel, urethra, ureter, esophagus, airway, bowel, nasal cavity, paranasal sinus, and the like) are caused to indwell in a treatment target site such as a stenosed site or the like. As an example of this treatment, a stent indwelling operation in percutaneous coronary intervention (PCI) is known.

According to the PCI, a stent is mounted on an outer surface of a balloon of a balloon catheter. The balloon is advanced along a guidewire so as to reach a treatment target site inside a blood vessel. Thereafter, the stent is detached from the balloon, and is caused to indwell in the treatment target site. For example, if a medical member is mounted on the balloon instead of the stent, a medical member can be delivered to a desired treatment target site in various biological organs in the same sequence as that of the stent indwelling operation in the related art. In addition, for example, even when the medical member is intended to indwell in a lumen such as a urethra, if a urethral dilating balloon catheter disclosed in Japanese Patent Application No. 8-526731 is diverted to other purposes, the medical member can be delivered to the desired site inside the urethra in the same sequence as that in the PCI.

When the balloon catheter in the related art is used, the balloon is positioned at the treatment target site by using an x-ray contrast marker or the like which is disposed in the balloon. However, it is not easy to arrange indwelling work in such a way that the balloon is positioned at the treatment target site by using the x-ray contrast marker and then the medical member is accurately positioned at the treatment target site. Consequently, it takes a lot of effort to carry out the indwelling work. In addition, after the medical member is arranged at the treatment target site, the balloon is dilated, and the medical member is pressed against the treatment target site. In this manner, the medical member can be prevented from being misaligned. However, if the balloon is not properly positioned at the treatment target site, uneven pressure is inevitably applied to each portion of the treatment target site. Thus, a sufficient holding force (fixing force) is not allowed to act thereon. As a result, the medical member is likely to be misaligned.

SUMMARY

A medical device is disclosed, which can relatively simply and quickly carry out work for delivering a medical member to a treatment target site after positioning, and which can improve operability of causing the medical member to indwell the treatment target site, and to provide a medical device assembly, a balloon device, and a treatment method for treating a urethral stricture.

According to the present disclosure, a medical device is disclosed for delivering a medical member, which is intended to indwell in a treatment target site inside a biological lumen. The medical device can include a flexible main body that extends in an axial direction, a balloon that can include an effectively dilatable portion on which the medical member is mounted, that has a dilating space into which a pressurizing medium flows between an outer surface of the main body and the balloon, and that is capable of dilating deformation and deflating deformation, an elongated guide member that is arranged across the treatment target site and the outside of a living body via the biological lumen, and an attachment portion to which at least a portion of the guide member is detachably attached at a position between both end portions in the axial direction of the main body. The main body is configured to be movable inside the biological lumen along a route having the guide member arranged therein, in a state where the guide member is attached to the attachment portion.

According to a medical device of the present disclosure, a balloon can be simply positioned at a treatment target site by using an elongated guide member arranged across the treatment target site and the outside of a living body via a biological lumen. The guide member holds a position of a main body during an indwelling operation. Accordingly, the balloon can be properly aligned. In addition, the guide member is attached to a position between both end portions in an axial direction of the main body of the medical device, that is, a position corresponding to a site where a pressurizing force (pressing force) is applied to the periphery when the balloon dilates. Therefore, an effectively dilatable portion, which can cause the pressurizing force to sufficiently act on the site, can be properly positioned at the treatment target site. In this manner, even when a medical member is intended to indwell in a meandering or curved site in the biological lumen, the pressurizing force can be prevented from being unevenly applied to each portion of the treatment target site, and the medical member can be properly prevented from being misaligned while the indwelling operation is performed.

DETAILED DESCRIPTION

Figure 1A:
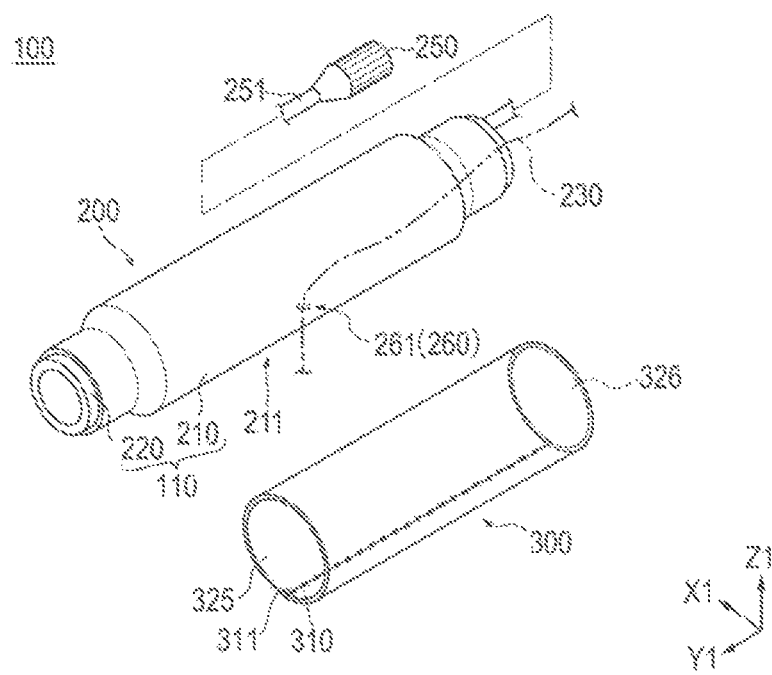
FIG. 1A is a perspective view of the medical device and the medical member after shaping according to a first embodiment of the present disclosure.

Hereinafter, an embodiment according to the present disclosure will be described with reference to each drawing. In some cases, dimensional proportions in the drawings may be exaggerated and different from actual proportions for convenience of description.

In the description of each embodiment, the medical device and the medical device assembly according to the present embodiment will be described through an example which is applied to treatment of a urethral stricture. First, a structure in the vicinity of the urethra of the living body, and a developmental mechanism or the like of the urethral stricture and restenosis will be described with reference to FIGS. 5A and 5B. The X-axis illustrated in each drawing represents a width direction (lateral direction in FIG. 5B) of the urethra, the Y-axis represents an extending direction (vertical direction in FIG. 5B) of the urethra, and the Z-axis represents a height direction (direction orthogonal to the paper surface of FIG. 5B) of the urethra.

Figure 5A:
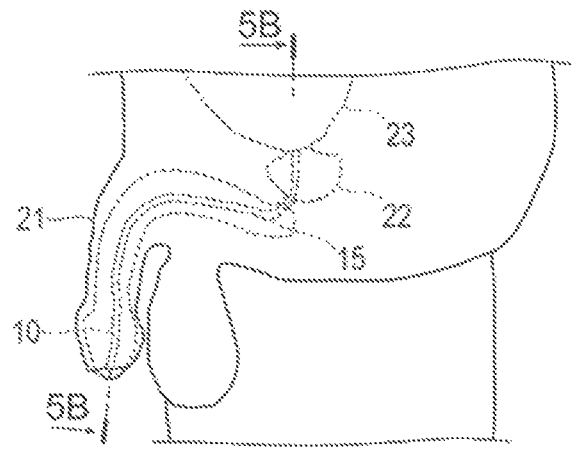
FIG. 5A is a view schematically illustrating the vicinity of a urethra of a living body.
Figure 5B:
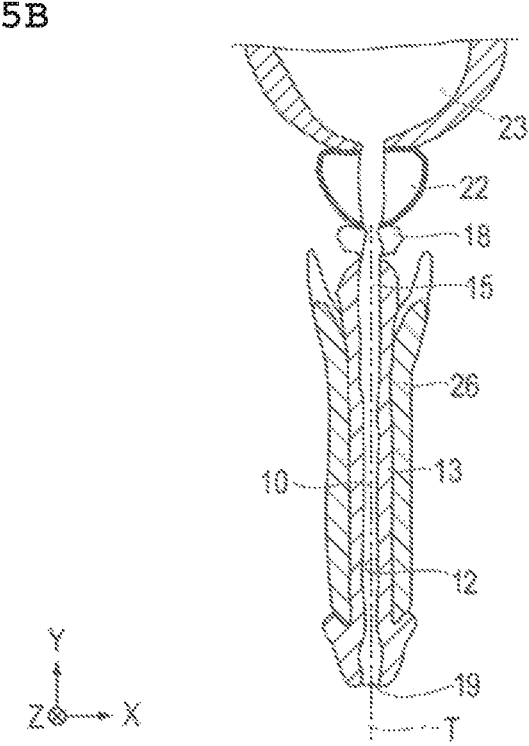
FIG. 5B is a sectional view taken along line 5B-5B (line along an extending direction of the urethra) illustrated in FIG. 5A.
Figure 6A:
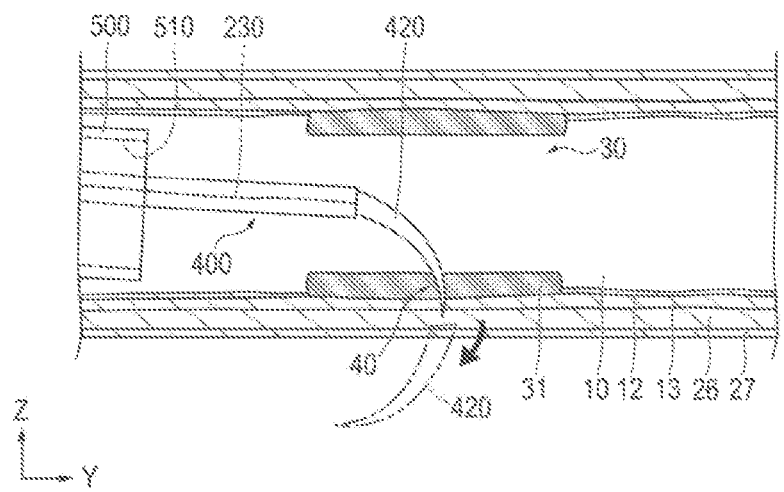
FIGS. 6A and 6B are sectional views for describing a use example and an operation of a medical device assembly (medical device and puncture tool) according to the first embodiment.

FIGS. 5A and 5B schematically illustrate a male urethra 10 and the peripheral portion. As illustrated in FIG. 5A, the urethra 10 extends to a bladder 23 located in a lower abdominal region of the living body through the inside of a penis 21 and the inside of a prostate 22. In addition, the urethra 10 has a bulbar urethra 15 present in front of an external urethra sphincter muscle 18. As illustrated in FIGS. 5B and 6A, an inner surface of the urethra 10 is covered with a urethral mucosa 12, and a corpus spongiosum 13 is present on the outer side of the urethral mucosa 12.

For example, the urethral stricture is a disease in which trauma or inflammation causes damage to the urethral mucosa 12 or the corpus spongiosum 13 and thereafter tissues suffer fibrosis and scarring in the urethral mucosa 12 or the corpus spongiosum 13 surrounding the urethral mucosa 12 during a process while the damage is recovered. As illustrated in FIG. 6A, a scar tissue 31 is formed on an inner surface of the urethra, and consequently, a lumen of the urethra 10 is narrowed. In a site (stenosed site 30) having the scar tissue 31 formed in the urethra 10, a cross-sectional area thereof is narrowed compared to other sites in the urethra 10. Consequently, urine is less likely to pass therethrough. If a person suffers from the urethral stricture, a urination disorder can occur in which the urine cannot be smoothly discharged or the urine cannot be completely discharged.

For example, as a treatment method for the urethral stricture, a treatment method has been attempted in which medical tools such as a bougie (urethra dilating tool), a balloon, a cold knife, a laser scalpel, and the like are transurethrally introduced into the urethra 10 through an external urethral orifice 19, and in which dilation, incision, or the like is performed on the stenosed site 30 by the medical tools. According to this method, a transient treatment effect can be obtained. However, after the treatment is performed once, there is a high possibility that the stenosed site 30 may be formed again, thereby causing the urethral stricture to recur. The reason for the occurrence of this restenosis can include the scar tissue 31 having a property, which allows a liquid to permeate therethrough. Accordingly, if the corpus spongiosum 13 located around the scar tissue 31 or under the scar tissue 31 is always exposed to the liquid (for example, urine or body fluid) flowing inside the urethra 10, persistent inflammatory reactions can be induced, thereby inhibiting regeneration of epithelial cells.

A medical device 200 and a medical device assembly according to the present embodiment are configured to function as a medical device which can be used when a medical member 300 is delivered and caused to indwell in order to prevent restenosis from occurring. Hereinafter, a configuration of each portion of the medical device 200 and the medical device assembly will be described.

Figure 2:
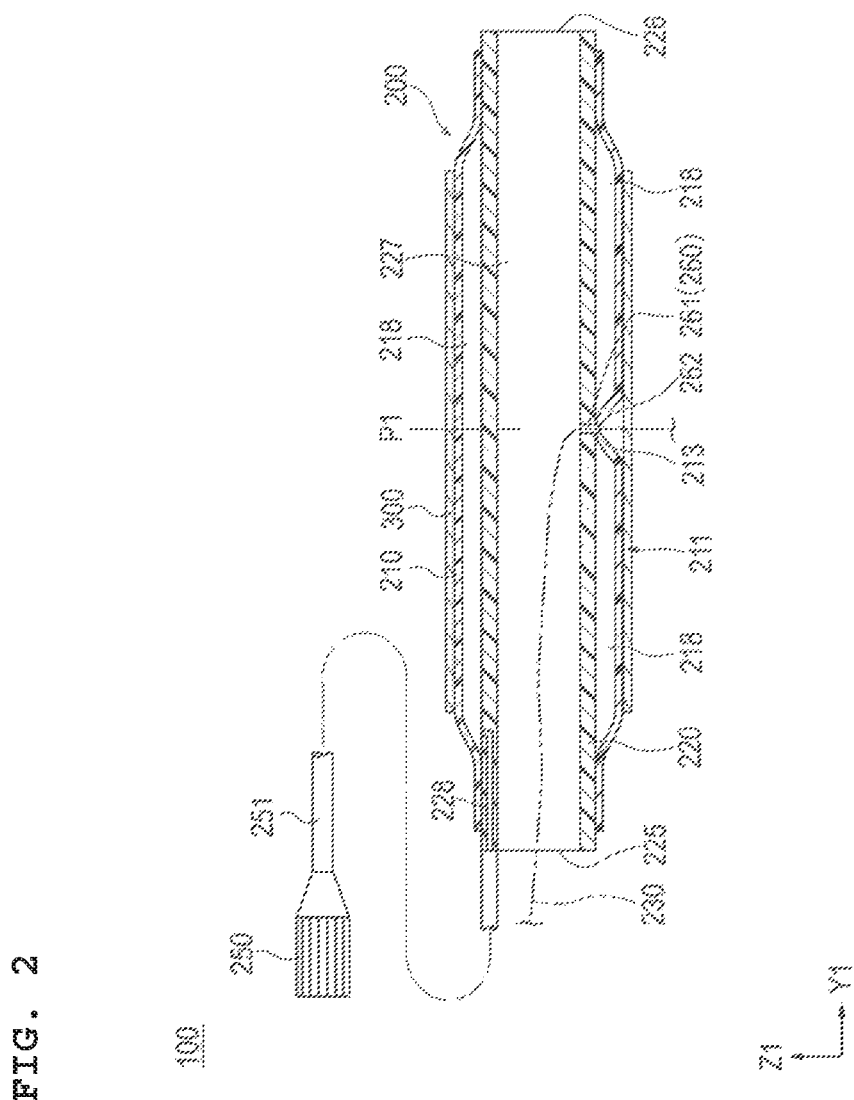
FIG. 2 is a partial sectional view illustrating the medical device according to the first embodiment.
Figure 7A:
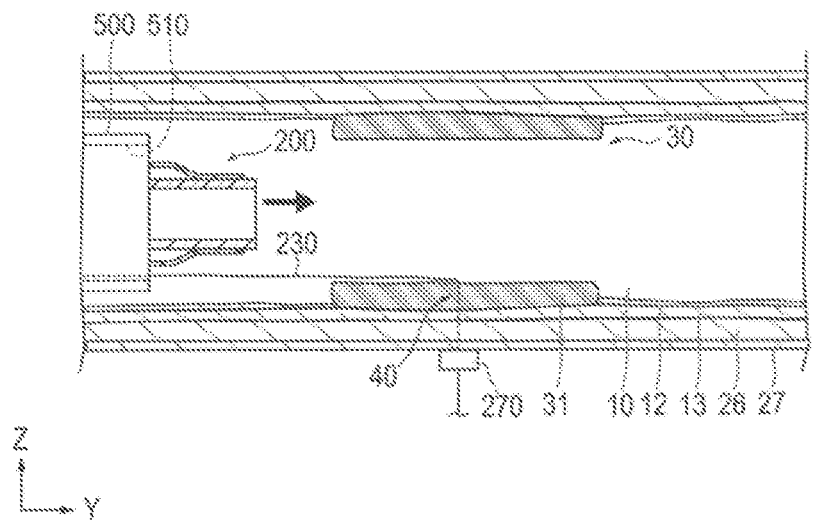
FIGS. 7A and 7B are sectional views for describing a use example and an operation of the medical device assembly (medical device and puncture tool) according to the first embodiment.
Figure 7B:
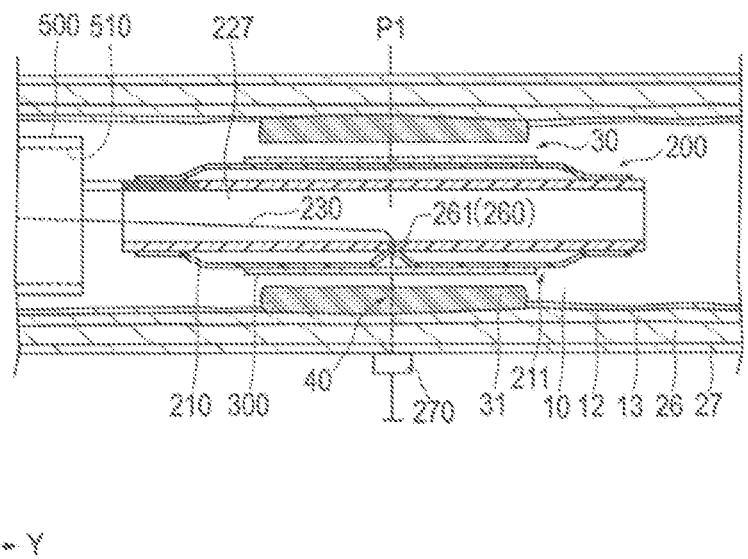

As illustrated in FIGS. 1A and 2, in brief, the medical device 200 has a flexible main body 220 that extends in an axial direction, a balloon 210 that can include an effectively dilatable portion 211 on which the medical member 300 is mounted, that has a dilating space 218 into which a pressurizing medium flows between an outer surface of the main body 220 and the balloon 210, and that is capable of dilating deformation and deflating deformation, an elongated guide member 230 that is arranged across a treatment site 40 which is a treatment target site and the outside of a living body via the urethra 10, and an attachment portion 260 to which a portion of the guide member 230 is detachably attached at a position between both end portions in the axial direction of the main body 220. Then, as illustrated in FIGS. 7A and 7B, the main body 220 is configured to be movable inside the urethra 10 via a route T (refer to FIG. 5B) having the guide member 230 arranged therein, in a state where the guide member 230 is attached to the attachment portion 260.

As illustrated in FIG. 1A, in the present embodiment, one in which the guide member 230 is added to a balloon device 110 configured to include the balloon 210 and the main body 220 is referred to as the medical device 200.

In the description, a side of the medical device 200 which is inserted into a living body is referred to as a distal side, and a predetermined connector port 250 side disposed in the medical device 200 is referred to as a proximal side. In addition, the X1 axis in the drawing represents a depth direction of the main body 220 of the medical device 200, the Y1 axis represents the axial direction (extending direction) of the main body 220 of the medical device 200, and the Z1 axis represents a height (thickness) direction of the main body 220 of the medical device 200.

As illustrated in FIG. 2, the main body 220 is configured to include a hollow member having a predetermined length in the axial direction. The main body 220 has a lumen 227 which extends in the axial direction, a proximal opening portion (corresponding to an opening portion) 225 which communicates with a proximal end of the lumen 227, a distal opening portion 226 which communicates with a distal end of the lumen 227, and a hole portion 261 which is formed so as to completely penetrate through the lumen 227.

The hole portion 261 is configured so that the guide member 230 can be inserted into the hole portion 261, and has a function as the attachment portion 260 for attaching the guide member 230 to the main body 220. The guide member 230 can be arranged so as to be introduced into the lumen 227 from the proximal opening portion 225 of the main body 220 and to be extracted to the outside of the lumen 227 through the hole portion 261. The guide member 230 is arranged so as to penetrate the inside of the main body 220 from the proximal opening portion 225 to the hole portion 261. In this manner, the guide member 230 is detachably attached to the main body 220.

A position for disposing the hole portion 261 (attachment portion 260) is not particularly limited as long as the position is between both end portions in the axial direction of the main body 220 of the medical device 200. However, in view of positioning of the balloon 210 at the treatment site 40, it can be preferable to dispose the hole portion 261 at a position where the hole portion overlaps the effectively dilatable portion 211 of the balloon 210 in the axial direction. In the medical device 200, the hole portion 261 is disposed in the vicinity of a central position P1 in the axial direction of the main body 220.

A distal portion and a proximal portion of the balloon 210 included in the medical device 200 are fixedly attached to the main body 220. As a method of fixedly attaching the balloon 210 to the main body 220, known methods such as bonding, welding, and the like can be employed in view of a configuration material of the balloon 210 and a configuration material of the main body 220.

The balloon 210 has an extracting portion 262 for extracting the guide member 230 which is extracted from the hole portion 261 of the main body 220 to an outer surface side of the balloon 210. The extracting portion 262 is configured to include a through-hole disposed in a thermally welded portion 213 formed by thermally welding a portion (portion substantially at the central position in the axial direction) of the balloon 210 to the periphery of the hole portion 261 of the main body 220. The thermally welded portion 213 is welded to the main body 220 so as to help ensure sealing performance to such an extent that a pressurizing medium does not leak out from the thermally welded portion 213.

A method for forming the extracting portion is not limited to the method of using the above-described thermal welding. For example, the extracting portion can be configured in such a way that a bonded portion (joint portion) including the same function as that of the thermally welded portion 213 is formed by means of photocoagulation or other known methods depending on the material of the main body 220 and the balloon 210, and that a through-hole or the like is properly formed in the bonded portion in a similar manner.

In accordance with an exemplary embodiment, the effectively dilatable portion 211 of the balloon 210 has a symmetrically dilated shape at the central position P1 in the axial direction of the main body 220. Therefore, when the balloon 210 dilates, an equal pressurizing force is applied from the central position P1 to the urethra 10 via the effectively dilatable portion 211 within a constant range on the distal side and the proximal side in the axial direction (refer to FIG. 8A). The effectively dilatable portion 211 can apply the pressurizing force to the outside when the balloon 210 dilates, and is configured to include portions other than the portion fixedly attached to the main body 220 and the portion thermally welded to the main body 220 (thermally welded portion 213) in the balloon 210.

A pressurizing medium flow path (lumen) 228, which communicates with the dilating space 218 can be disposed inside a proximal side wall of the main body 220. A predetermined tube 251 through which a pressurizing medium such as a liquid and gas can flow is connected to the pressurizing medium flow path 228 in a liquid-tight and an air-tight manner. A connector port 250 is attached to a proximal portion of the tube 251. The connector port 250 is configured so that a known Indeflator or the like in the medical field can be interlocked with and detachable from the connector port 250. The pressurizing medium is caused to flow into the dilating space 218 via the connector port 250, the tube 251, and the pressurizing medium flow path 228, thereby enabling the balloon 210 to be dilated and deformed. In addition, the pressurizing medium is discharged from the inside of the dilating space 218, thereby enabling the balloon 210 to be deflated and deformed.

The main body 220 can be configured to include a flexible material. For example, a configuration material of the main body 220 can include polyesters such as polyvinyl chloride, polyethylene, polypropylene, cyclic polyolefin, polystyrene, poly (4-methylpentene-1), polycarbonate, acrylic resin, polyethylene terephthalate, polyethylene naphthalate, and the like, various soft or hard resins such as butadiene-styrene copolymers, polyamides (for example, nylon 6, nylon 6.6, nylon 6.10, nylon 12), various rubber materials such as natural rubber, butyl rubber, isoprene rubber, butadiene rubber, styrene-butadiene rubber, and silicone rubber, various thermoplastic elastomers such as polyurethane system, polyester system, polyamide system, olefin system, styrene system, and the like, various metal materials such as stainless steel, aluminum, copper or a copper-based alloy, and the like, or various ceramics such as various types of glass, alumina, silica, and the like. When the hard resin, metal, and ceramic are used as the configuration material of the main body 220, it is possible to adjust properties so as to have desired elasticity (flexibility) by properly performing laser processing or the like.

For example, the main body 220 can be configured so that the main body 220 can be dilated and deformed inward in a radial direction (axial direction of the main body 220) in response to the pressurizing medium flowing into the dilating space 218 partitioned between the main body 220 and the balloon 210. According to this configuration, when the main body 220 is introduced into the urethra 10, the main body 220 is dilated and deformed in a state where a predetermined guiding tool (for example, a bougie for a urethra, a rod-shaped insertion tool, an endoscope, or the like) is inserted into the lumen 227 of the main body 220. Accordingly, the guiding tool can be held with respect to the main body 220. In this manner, work for introducing the main body 220 into the urethra 10 can be performed by using the guiding tool. Accordingly, it is possible to more smoothly introduce the main body 220. For example, as a method of configuring the main body 220 to be capable of dilating deformation, it is possible to employ a method of adjusting a wall thickness or a configuration material of the main body 220, a method of attaching a film material or the like which partitions the dilating space 218 communicating with the pressurizing medium flow path 228 inside the main body 220, or the like.

A configuration material of the balloon 210 is not particularly limited. However, for example, the same material as that of a balloon used for a medical balloon catheter can be used. As an example, the configuration material can include polyolefin such as polyethylene, polypropylene, ethylene-propylene copolymer, and the like, polyesters such as polyethylene terephthalate, and the like, thermoplastic resins such as polyvinyl chloride, ethylene-vinyl acetate copolymer, cross-linked ethylene-vinyl acetate copolymer, polyurethane, and the like, polyamide elastomer, polystyrene elastomer, silicone rubber, latex rubber, or the like. In addition, the balloon 210 may be formed to have a single-layer structure using these materials, or may be formed to have a laminated structure of two or more layers.

In accordance with an exemplary embodiment, the guide member 230 is configured to include a biocompatible material. For example, the guide member 230 can be configured to include thermoplastic elastomers such as polyvinyl chloride, polyurethane elastomer, polystyrene elastomer, styrene-ethylene-butylene-styrene copolymer (SEBS), styrene-ethylene-propylene-styrene copolymer (SEPS), and the like, thermoplastic resins such as nylon, PET, and the like, poly-dioxane (PDS), polylactic acid, polyglycolic acid, biodegradable resin made of these copolymers, and the like, or thermosetting resins such as rubber, silicone elastomer, and the like, fiber materials such as silk, cotton yarn, cellulose fiber, and the like, metal materials such as SUS wire, copper wire, titanium wire, nitinol wire and the like, or a proper combination of these materials.

In accordance with an exemplary embodiment, each dimension such as the length, the outer diameter, and the like of the guide member 230 can be set to a desired dimension depending on the length of a biological lumen which is an application target of the medical device 200, and an individual difference of a patient, or the like. A sectional shape of the guide member 230 may be any shape among a circular shape, an elliptical shape, a rectangular shape, and the like. In addition, the sectional shape is not particularly limited to these shapes.

As illustrated in FIG. 1A, the medical device 200 and the medical member 300 configure a treatment device 100 used in treating the urethral stricture.

As the medical member 300 used in treating the urethral stricture, oral mucosa (epithelium) collected from a living body can be used (for example, a human body). The oral mucosa can include an epithelial cell, and an epithelial function can be provided (granted and acquired) by engrafting the epithelial cell. The oral mucosa can protect the treatment site 40 from a liquid such as urine by forming the epithelial cell (urethral mucosa) which consistently prevents the urine from permeating.

Figure 1B:
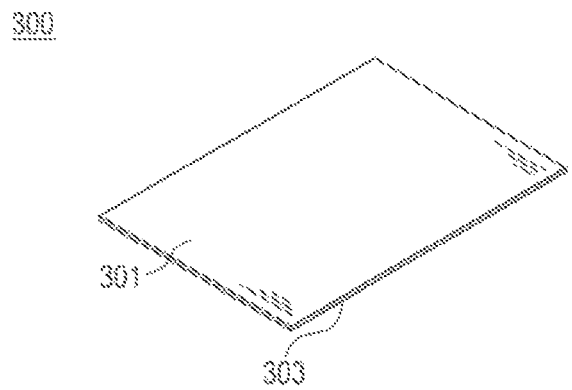
FIG. 1B is a perspective view of the medical member before shaping according to the first embodiment of the present disclosure.

As illustrated in FIG. 1B, for example, the medical member 300 can employ those, which are configured as a rectangular sheet-like member including a front surface 301 and a rear surface 303. When the medical member 300 is introduced into the living body, the medical member 300 is shaped (re-shaped) into a cylindrical shape as illustrated in FIG. 1A. Then, the main body 220 together with the balloon 210 is inserted into the inside of the medical member 300 via a distal opening portion 325 or a proximal opening portion 326 which is formed in the medical member 300. In this manner, the medical member 300 can be externally mounted on an outer surface of the effectively dilatable portion 211 of the balloon 210. Before work is carried out in order to shape the medical member 300 into a cylindrical shape, the medical member 300 can be externally mounted by winding the medical member 300 around the outer surface of the balloon 210.

As illustrated in FIG. 1A, for example, an end side 310 of the medical member 300 can be fixed by means of suturing or the like so that the medical member 300 can maintain the cylindrical shape. In the illustrated example, a suture thread 311 is used for fixing. For example, as the suture thread, a known biocompatible suture thread can be used. It is preferable to dispose a gap at the location sutured using the suture thread 311 to such an extent that the guide member 230 can be inserted into the gap. When the medical member 300 is introduced into the urethra 10, the guide member 230 can be pulled out to the outer surface of the medical member 300 by disposing this gap.

A configuration, a material, and the like of the medical member 300 are not particularly limited as long as the medical member 300 can provide the epithelial function by being introduced into the biological lumen which is the treatment target. The outer shape and properties when not in use, the outer shape and properties when externally mounted on the main body 220, the fixing method, the thickness, and the outer dimension of the end side 310, can be appropriately changed. In addition, for example, the other one in addition to the oral mucosa can be used as the medical member 300. It is possible to use other epithelium collected from the living body or those which are obtained by fixing the epithelial cell to a thin film member having a sheet shape. In addition, the medical member 300 may be a member configured to include an agent, gel, micro beads, and a synthetic polymer, which promote the regeneration of the epithelial function, or a member configured to include a material serving to replace the recovery of the epithelial function.

Next, a puncture tool 400 used according to the present embodiment will be described with reference to FIGS. 3A, 3B, 4A, and 4B.

The puncture tool 400 is used in order to properly arrange the guide member 230 inside and outside the urethra 10. In addition, the puncture tool 400 can be used in combination with the medical device 200 or the treatment device 100, and configures the medical device assembly used in treating the urethral stricture together with the medical device 200 or the treatment device 100.

The puncture tool 400 has a puncture needle 420 to which the guide member 230 is attached so as to be connectable and detachable, a main body 410 including a lumen 417 into which the guide member 230 is inserted, and a hub 430 having a lock mechanism 435, which can switch fixing and unfixing the guide member 230.

In accordance with an exemplary embodiment, the puncture needle 420 is configured to include a curved needle having a predetermined curvature. A fixing member 440, which comes into contact with a proximal portion 421 of the puncture needle 420 is arranged inside the main body 410 of the puncture tool 400. This fixing member 440 can regulate the position of the proximal portion 421 of the puncture needle 420 so as not to unnecessarily enter the inside of the main body 410. A shape, a material, and the like of the puncture needle 420 are not particularly limited as long as the puncture needle 420 can puncture a biological lumen (for example, the urethra 10) for treatment. For example, as will be described in the embodiment, it is also possible to use a straight needle 960 or the like in which the needle entirely has a linear shape (refer to FIG. 19).

Figure 4A:
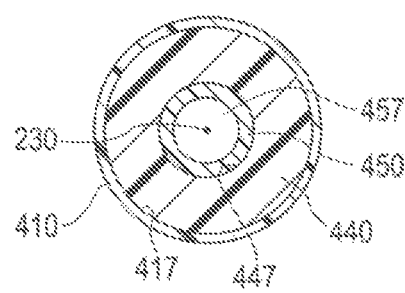
FIG. 4A is a sectional view of the puncture tool taken along line 4A-4A illustrated in FIG. 3B.
Figure 4B:
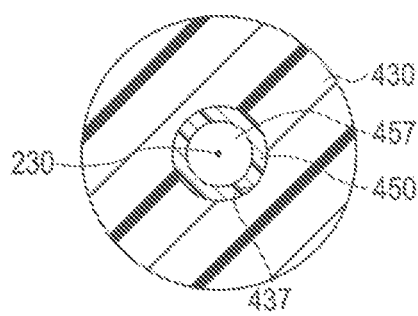
FIG. 4B is a sectional view of the puncture tool taken along line 4B-4B illustrated in FIG. 3B.

In accordance with an exemplary embodiment, a predetermined tubular member 450 is inserted into the main body 410 of the puncture tool 400. The guide member 230 is arranged so as to be inserted into a lumen 457 of the tubular member 450. As illustrated in FIG. 4A, a lumen 447 into which a distal portion of the tubular member 450 is inserted is formed in the fixing member 440. In addition, as illustrated in FIG. 4B, the lumen 457 into which a proximal portion of the tubular member 450 is inserted is formed in the hub 430. The tubular member 450 is arranged so that the distal portion comes into pressurizing contact with an inner surface of the fixing member 440, and is arranged so that the proximal portion comes into pressurizing contact with an inner surface of the hub 430. In this manner, the tubular member 450 is fixed to the main body 410.

Figure 3A:
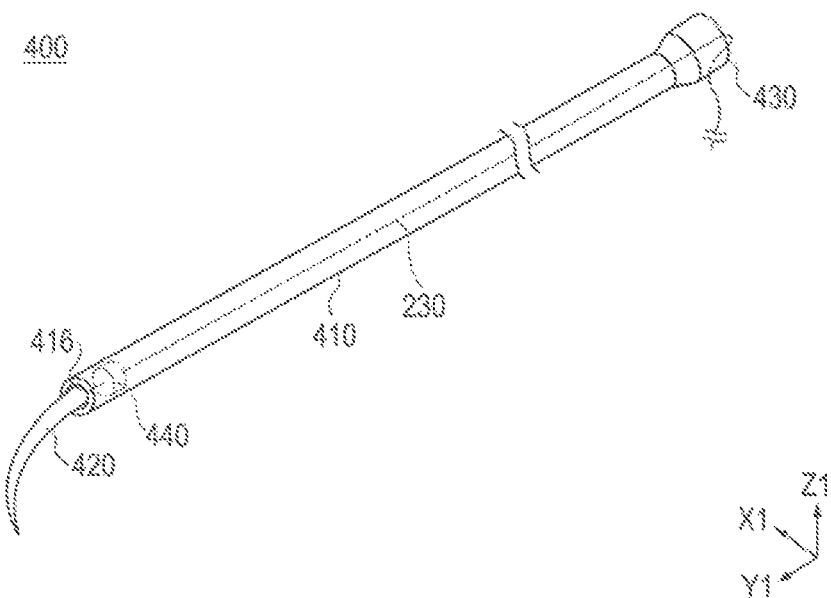
FIG. 3A is a perspective view of a puncture tool according to the first embodiment.
Figure 3B:
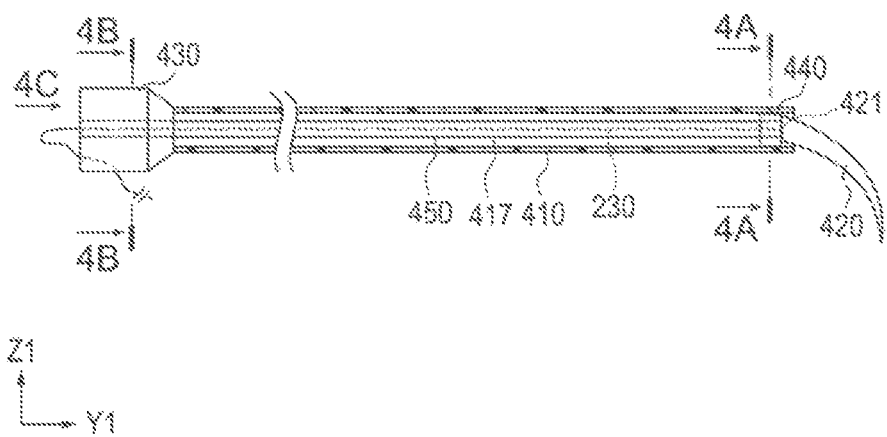
FIG. 3B is a partial sectional view of the puncture tool according to the first embodiment.
Figure 4C:
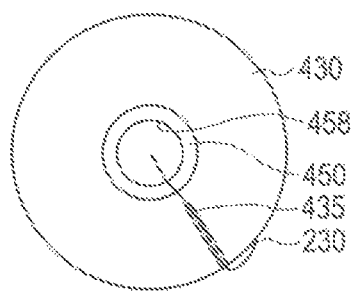
FIG. 4C is an arrow view when viewed in a direction of an arrow 4C illustrated in FIG. 3B.

As illustrated in FIG. 3B, the distal portion of the guide member 230 is attached to an end surface of the proximal portion 421 of the puncture needle 420. As illustrated in FIG. 4C, the proximal portion of the guide member 230 is extracted outward from the hub 430 via a proximal opening portion 458 of the tubular member 450. The proximal portion of the guide member 230 extracted outward from the hub 430 is fixed to the hub 430 by the lock mechanism 435. In this manner, it is possible to prevent each inadvertent movement of the guide member 230 and the puncture needle 420 which is connected to the guide member 230. A configuration of the lock mechanism 435 is not particularly limited. However, according to the present embodiment, a slit formed in the hub 430 is utilized as the lock mechanism. The slit is configured to have a width which is approximately the same as or smaller than the outer diameter of the guide member 230. The guide member 230 is pressed and inserted into the slit, and the guide member 230 is brought into pressurizing contact with an inner surface of the slit. In this manner, the guide member 230 can be fixed.

For example, the puncture tool 400 can be configured so that the fixing member 440 is relatively slidable with respect to the main body 410 in the axial direction inside the lumen 417 of the main body 410. According to this configuration, the puncture needle 420 can be temporarily accommodated inside the lumen 417 of the main body 410. Therefore, when the puncture needle 420 is delivered to a treatment site, it is possible to reduce risks in which the puncture needle 420 may erroneously puncture a biological tissue, for example.

For example, the puncture needle 420 of the puncture tool 400 can be configured to include a metal material or a hard resin material. A material of the other respective members configuring the puncture tool 400 is not particularly limited. However, for example, the puncture tool 400 can be configured to include a known resin material or the like.

Next, an example of manual skills by which the medical device 200 is used will be described with reference to FIGS. 6A to 8B.

First, predetermined treatment is performed on the stenosed site 30 formed in the urethra 10. For example, the treatment can include treatment for incising the scar tissue 31. In the description of the embodiment, a site where the predetermined treatment is performed on the stenosed site 30 and a peripheral site thereof (including the scar tissue 31 present in the periphery) are referred to as the treatment site 40 for the sake of convenience (refer to FIGS. 6A and 6B). For example, as a treatment tool used for treatment, it is possible to use a known cold knife, laser scalpel, or the like which is used for incision, ablation, or the like of tissues. When the treatment is performed, the treatment can be progressively performed while a state inside the urethra 10 is confirmed by using a rigid endoscope such as a bladder endoscope and the like. For example, a known flexible endoscope can be used in order to observe the inside of the urethra 10.

Next, as illustrated in FIG. 6A, the puncture tool 400 is introduced into the urethra 10. For example, the puncture tool 400 is moved to the vicinity of the stenosed site 30 through a channel 510 of a known rigid endoscope 500. Then, the puncture needle 420 of the puncture tool 400 is caused to pierce the treatment site 40. The piercing position is not particularly limited. However, the position of the medical device 200 when the medical member 300 is caused to indwell depends on the piercing position. Therefore, while the piercing position is confirmed by using the rigid endoscope 500 during the piercing, it is preferable to progressively carry out the work by pre-setting the piercing position to a proper position prior to the treatment.

Figure 6B:
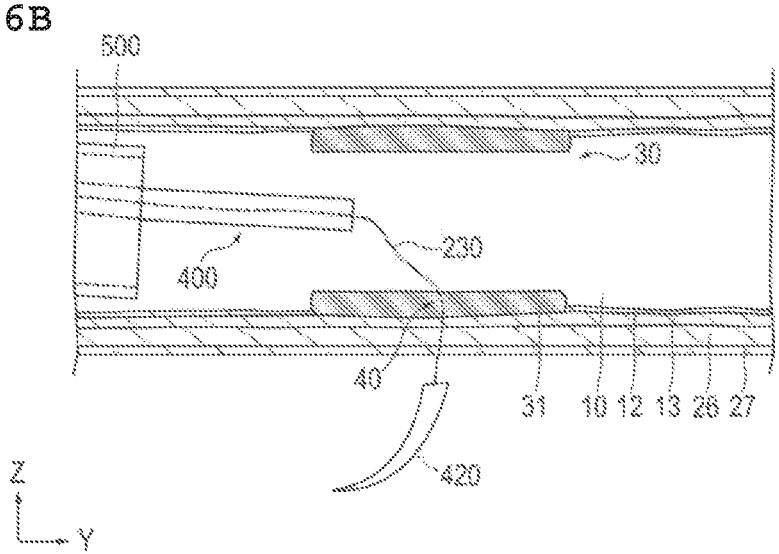

As illustrated in FIG. 6B, the puncturing is performed until the puncture needle 420 penetrates through an outer skin 27 of the penis 21. While the piercing position is confirmed using the rigid endoscope 500, the puncturing is performed from the inside of the urethra 10. Accordingly, even when the treatment is performed on the bulbar urethra 15 or the like, it is possible to prevent the puncturing from being erroneously performed on the bladder 23, the external urethra sphincter muscle 18, or the like.

The puncture needle 420 penetrates through the outer skin 27, and the guide member 230 is extracted outward from the urethra 10. Thereafter, the lock mechanism 435 (refer to FIG. 4C) unlocks the guide member 230. If the guide member 230 is unlocked, the hub 430 of the puncture tool 400 and the guide member 230 are unfixed. Accordingly, the hub 430 and the guide member 230 are detached from each other, thereby enabling both members to be operated independently from each other. The hub 430 of the puncture tool 400, or the main body 410 is properly removed from the urethra 10 after the puncture work is carried out.

Next, the guide member 230 and the puncture needle 420 are detached from each other. For example, both of these are detached by cutting the guide member 230. The distal end side (end portion side connected to the puncture needle 420) of the guide member 230 is extracted outward from the living body by a predetermined amount of length after penetrating through the treatment site 40. In accordance with an exemplary embodiment, the proximal side of the guide member 230 is extracted outward from the living body by a predetermined amount of length by way of the urethra 10 and the external urethral orifice 19.

In this case, as illustrated in FIG. 7A, it is possible to restrict mobility of the guide member 230 extracted outward from the urethra 10 by using a predetermined stopper 270. A configuration of the stopper 270 is not particularly limited. However, for example, it is possible to use a simple structure configured to prevent the guide member 230 from being inadvertently moved due to a friction force generated between the inner surface of the slit and the guide member 230 by fitting the guide member 230 into the slit formed in the stopper 270. The mobility of the guide member 230 can be suppressed by arranging the stopper 270 in the lumen 227 of the main body 220 of the medical device 200, or the mobility of the guide member 230 can also be suppressed by arranging the stopper 270 in both the outside of the main body 220 and the lumen 227.

Figure 17A:
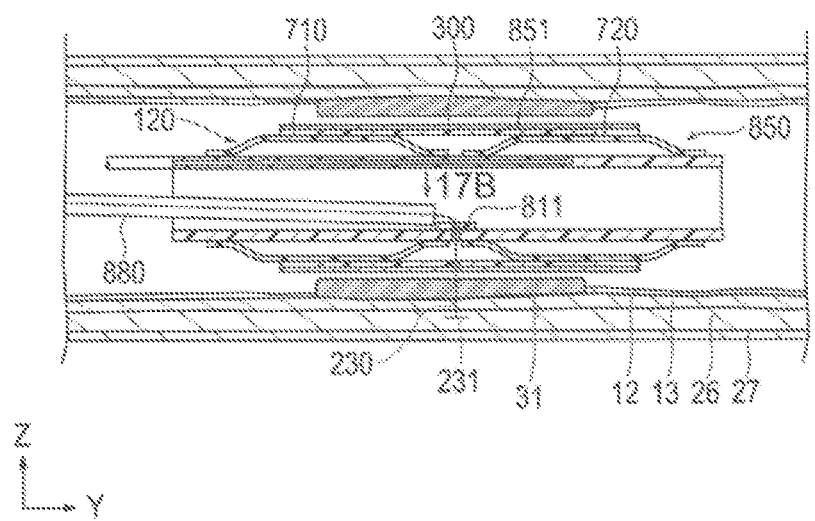
FIG. 17A is a view illustrating a procedure for introducing the medical device according to the second embodiment into a living body, and which illustrates a sectional view illustrating a work procedure.

For example, without being extracted outward from the living body, the distal portion of the guide member 230 can also be caused to indwell in the wall (corpus spongiosum penis 26 or the like) of the urethra 10 (refer to FIG. 17A). In addition, when the guide member 230 indwells in the inside of the wall of the urethra 10, in order to prevent the guide member 230 from being inadvertently moved or being pulled out therefrom, it is possible to form a knot 231 or to form a predetermined locking member or the like in the distal end of the guide member 230, for example.

Next, as illustrated in FIGS. 1A and 2, the guide member 230 arranged outside the external urethral orifice 19 is attached to the medical device 200. Then, as illustrated in FIG. 7A, the medical device 200 is introduced into the urethra 10 along the guide member 230. The medical device 200 moves toward the stenosed site 30 while tracing the route T (refer to FIG. 5B) formed by the guide member 230 arranged from the external urethral orifice 19 to the treatment site 40 which is the treatment target site. In this case, while the proximal portion of the guide member 230 is gripped or fixed to a predetermined position outside the living body, work is carried out in order to press the medical device 200 into the urethra 10 by using a guiding catheter or the like. In this manner, the medical device 200 can be smoothly moved.

The route T formed by the guide member 230 can be appropriately changed depending on a state where the guide member 230 is arranged (bent state, state of being pulled and extended in a substantially linear shape, or the like). However, if the guide member 230 forms at least a moving route of the medical device 200 which connects the outside of the urethra 10 and the treatment site 40, a function to guide the movement (delivery) of the medical device 200 is not impaired.

If the work for introducing the medical device 200 is continuously carried out and the medical device 200 is moved along the guide member 230, as illustrated in FIG. 7B, the central position P1 of the main body 220 of the medical device 200 can be positioned in the vicinity of the position where the puncture needle 420 punctures the treatment site 40.

Figure 8A:
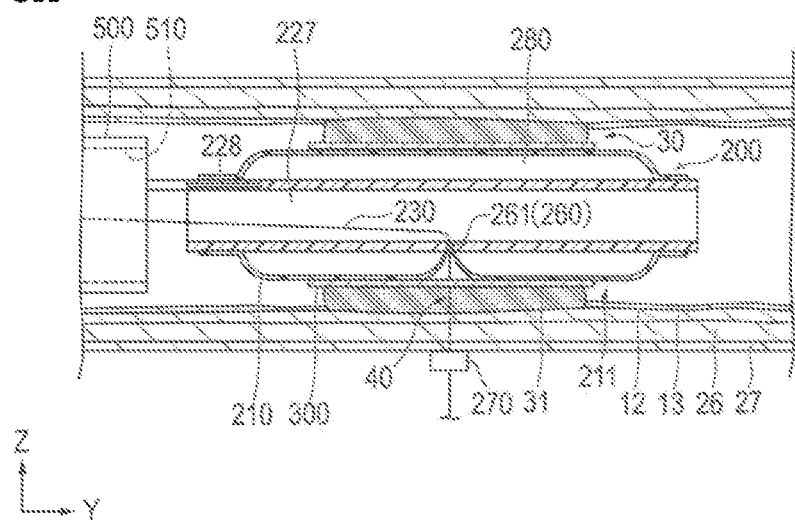
FIGS. 8A and 8B are sectional views for describing a use example and an operation of the medical device assembly (medical device and puncture tool) according to the first embodiment.

As illustrated in FIG. 8A, after the medical device 200 is properly positioned and arranged, the balloon 210 can be dilated. In this manner, the medical member 300 is pressed against the treatment site 40 via the effectively dilatable portion 211 of the balloon 210. By maintaining a state where the balloon 210 dilates, a state where the medical member 300 is in contact with the treatment site 40 can be properly maintained. In addition, the medical member 300 indwells in a state where the guide member 230 is caught on the attachment portion 260. Accordingly, there is no possibility that the medical device 200 may be separated from and greatly misaligned with the guide member 230. Therefore, the positioned state can be stably maintained.

Figure 8B:
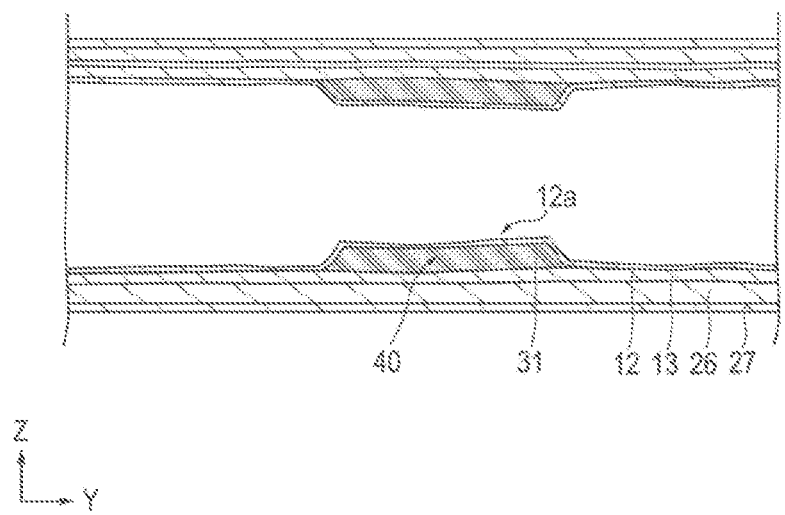

As illustrated in FIG. 8B, if the medical member 300 indwells in the inside of the urethra 10 over a predetermined period of time, a portion of the medical member 300 (both end portions on the distal side and the proximal side in the illustrated example) can be integrated with the epithelium of the urethral mucosa 12. In this manner, the medical member 300 and the urethral mucosa 12 in the vicinity thereof form a new urethral mucosa layer 12a which covers the scar tissue 31 (portion where the scar tissue 31 is formed if the scar tissue 31 does not remain). Accordingly, the treatment site 40 can be provided with the epithelial function. When the medical member 300 is configured to include a medical member other than the member engrafted into the living body like the epithelium, the medical member is fixed to the treatment site 40 (stays in the vicinity of the treatment site 40), thereby providing the treatment site 40 with the epithelial function.

After the medical member 300 is engrafted, the medical device 200 is removed from the inside of the urethra 10. At this time, the balloon 210 is deflated to have a size removable from the urethra 10. The amount of dilating deformation of the balloon 210 can be appropriately adjusted during a period while the medical device 200 indwells so as not to apply a relatively excessive burden on a patient.

Through the above-described procedures, an operator completes the manual skills for suppressing the recurrence of the urethral stricture, in which the medical member 300 is introduced into the urethra 10, the medical member 300 is caused to indwell in the treatment site 40, and the medical member 300 provides the treatment site 40 with the epithelial function.

The above-described treatment method for the urethral stricture can include a forming process of forming the treatment site by performing predetermined treatment on the scar tissue formed in the urethra, an arrangement process of arranging the elongated guide member at the treatment site via the urethra, a delivery process of delivering the medical device including the balloon having the medical member mounted thereon to the treatment site along the guide member, and an indwelling process of causing the medical member to indwell over a predetermined period of time by dilating the balloon positioned at the treatment site and maintaining a state where the medical member is brought into contact with the treatment site. In addition, the arrangement process can include an inserting process of inserting the guide member into the outside of the urethra from the inside of the urethra. In addition, the inserting process can include a pulling-out process of pulling the guide member out from the urethra by causing the puncture tool having the guide member attached thereto to puncture the urethra from the inside of the urethra to the outside of the urethra. In addition, the arrangement process can include a connecting process of connecting the guide member and the stopper to each other outside the urethra.

As described above, according to the medical device 200 in the present embodiment, the balloon 210 can be positioned at the treatment site 40 by using the elongated guide member 230 arranged across the treatment site 40 (treatment target site) and the outside of the living body via the urethra 10. The guide member 230 holds the position of the main body 220 when the balloon 210 indwells. Accordingly, the balloon 210 can be properly aligned. In addition, the guide member 230 is attached to a position between both end portions in the axial direction of the main body 220 of the medical device 200, that is, a position corresponding to a portion where a pressurizing force (pressing force) is applied to the periphery of the balloon 210 when the balloon 210 dilates. Accordingly, the effectively dilatable portion 211, which can cause the pressurizing force to sufficiently act thereon can be properly positioned at the treatment site 40. In this manner, even when the medical member 300 is intended to indwell in a meandering or curved site (for example, the bulbar urethra 15 or the like) in the biological lumen, the pressurizing force can be prevented from being unevenly applied to each portion of the treatment site 40, and the medical member 300 can be prevented from being misaligned while the indwelling operation is performed.

In addition, by preventing the pressurizing force of the balloon 210 from being unevenly applied, an excessive pressurizing force can be prevented from being intensively applied to a portion of the inner wall of the urethra 10, compared to the other portions in the treatment site 40. Therefore, the occurrence of necrosis, inflammation or the like can be prevented.

In addition, the main body 220 has the lumen 227 which extends in the axial direction, the proximal opening portion 225 for inserting the guide member 230 into the lumen 227, and the hole portion 261 which extracts the guide member 230 from the lumen 227 to the outside of the main body 220. The balloon 210 has the extracting portion 262 for extracting the guide member 230 extracted from the hole portion 261 to the outer surface side of the balloon 210. Accordingly, the guide member 230 can be easily extracted to the outside of the main body 220 and to the outside of the balloon 210. Therefore, the medical device 200 can be smoothly moved along the guide member 230 in a state where the main body 220 is caught on the guide member 230.

In addition, the extracting portion 262 is configured to include the through-hole disposed in the thermally welded portion 213 formed by thermally welding a portion of the balloon 210 to the periphery of the hole portion 261 of the main body 220. Accordingly, without degrading the airtightness of the dilating space 218 of the balloon 210, the guide member 230 can be extracted to the outer surface side of the main body 220 and the balloon 210.

In addition, the attachment portion 260 is disposed in the vicinity of the central position in the axial direction of the main body 220, and the effectively dilatable portion 211 of the balloon 210 has a symmetrically dilated shape at the central position in the axial direction of the main body 220. Accordingly, the central position of the effectively dilatable portion 211 can be arranged by being positioned at the treatment site 40, and a relatively more uniform pressurizing force can be applied in the extending direction of the treatment site 40.

In addition, the stopper 270 is disposed inside the main body 220 and/or outside the main body 220 so as to restrict mobility of the guide member 230. Accordingly, the medical device 200 can be prevented from being inadvertently moved while the work for delivering the medical device 200 is carried out or in a state where the medical device 200 indwells. Therefore, the misalignment of the medical device 200 can be prevented.

In addition, the medical member 300 is configured to include a sheet-like member which provides the biological tissue with the epithelial function, and is introduced into the urethra 10 in a state where the medical member 300 is wound around the effectively dilatable portion 211 of the balloon 210 in the circumferential direction. Accordingly, the work for introducing the medical member 300 into the living body can be facilitated and can be carried out in a less invasive manner. Furthermore, the epithelial cell can be engrafted in the treatment site 40 by utilizing the epithelial tissue. Therefore, a treatment effect using the medical member 300 can be improved.

In addition, the medical device assembly can be provided that has the puncture tool 400 including the puncture needle 420 to which the guide member 230 is attached so as to be connectable and detachable, the main body 410 including the lumen 417 into which the guide member 230 is inserted, the hub 430 having the lock mechanism 435 which can switch fixing and unfixing of the guide member 230, and the medical device 200, and that can simply and quickly deliver the medical member 300 and cause the medical member 300 to indwell.

In addition, it is possible to provide the balloon device 110 which has the balloon 210 and the main body 220, and which is configured so that the guide member 230 inserted into the lumen 227 of the main body 220 can be easily extracted to the outer surface side of the balloon 210.

Next, a modification example of the above-described first embodiment will be described. In the description of the modification example, with regard to the same member as the previously described member or the element, which can be similarly configured, description thereof will be appropriately omitted.

Figure 9A:
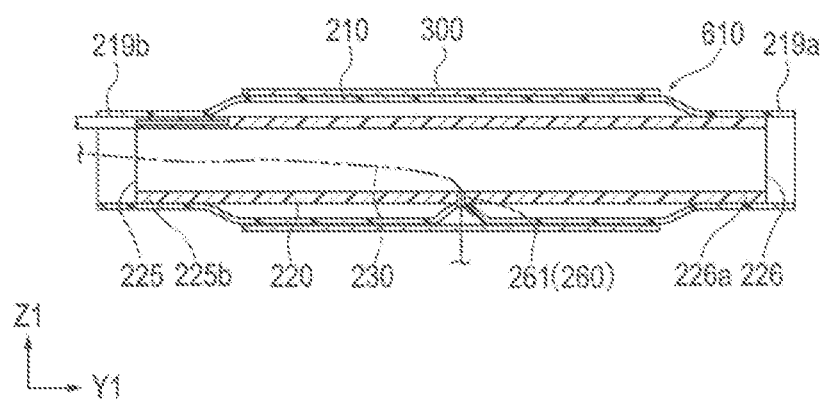
FIG. 9A is a partial sectional view illustrating a medical device according to a modification of the first embodiment, Modification Example 1.

FIG. 9A illustrates a medical device 610 according to Modification Example 1 of the first embodiment.

In the medical device 610, a distal side end portion 226a of the main body 220 is covered with a distal side end portion 219a of the balloon 210, and a proximal end portion 225b of the main body 220 is covered with a proximal side end portion 219b of the balloon 210. According to this configuration, when the medical device 610 is introduced into the urethra 10, both end portions 225a and 226a of the main body can be prevented from rubbing against the inner wall of the urethra 10. Therefore, it is possible to realize less invasive manual skills.

Figure 9B:
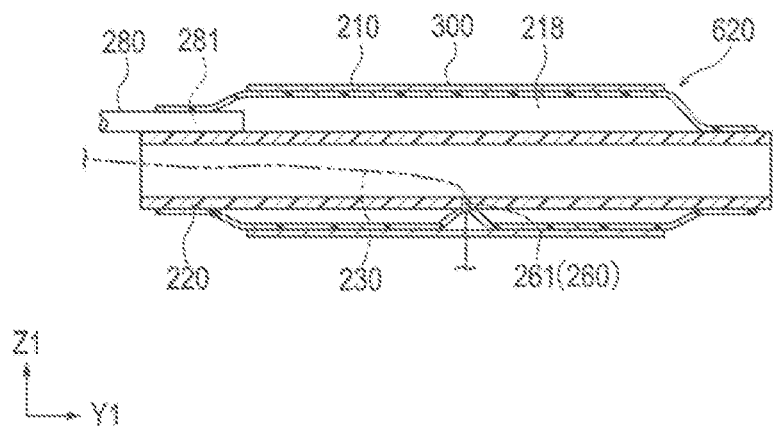
FIG. 9B is a partial sectional view illustrating a medical device according to a modification of the first embodiment, Modification Example 2.

FIG. 9B illustrates a medical device 620 according to Modification Example 2 of the first embodiment.

In the medical device 620, a tube 280, which supplies a pressurizing medium to the dilating space 218 of the balloon 210 is directly attached so as to face the inside of the dilating space 218. Even when the tube 280 is used, similarly to when the pressurizing medium supply flow path 228 formed inside the wall of the main body 220 is used as described above, the balloon 210 can be operated so as to be dilated and deflated by supplying and discharging the pressurizing medium via a flow path 281 of the tube 280.

Next, a medical device according to a second embodiment of the present disclosure will be described. In the description of the second embodiment, with regard to the same member as the previously described member, the element which can be similarly configured, the similar treatment procedure (procedure in the manual skills), or the like, description thereof will be appropriately omitted.

Figure 10:
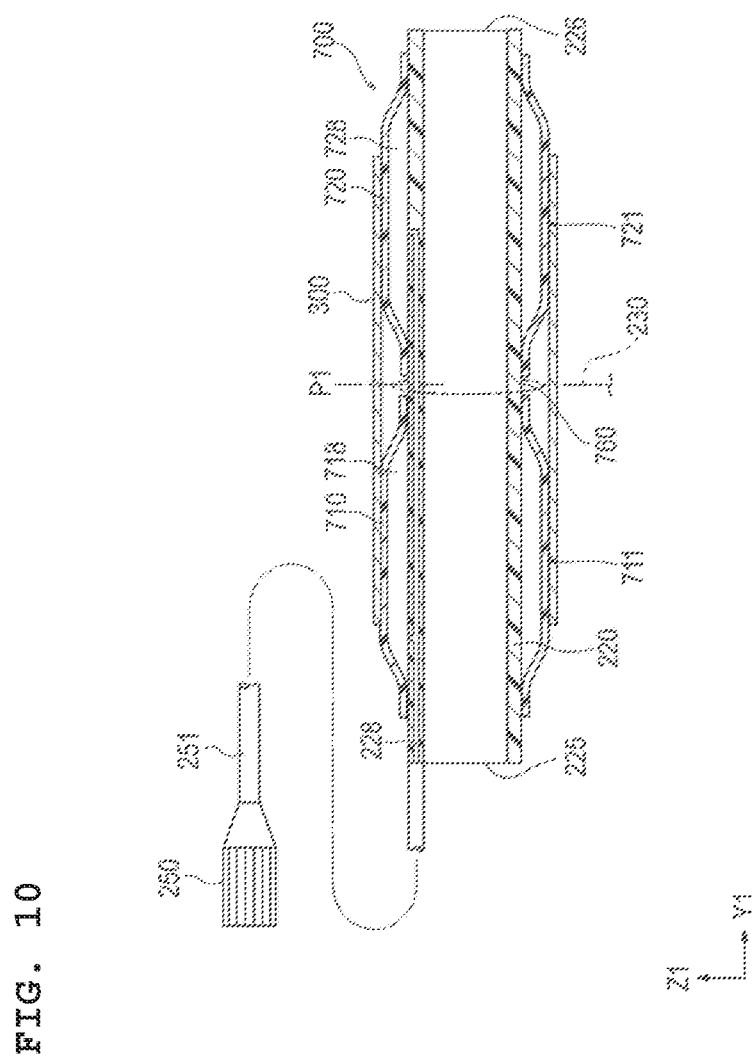
FIG. 10 is a partial sectional view illustrating a medical device according to a second embodiment.
Figure 11A:
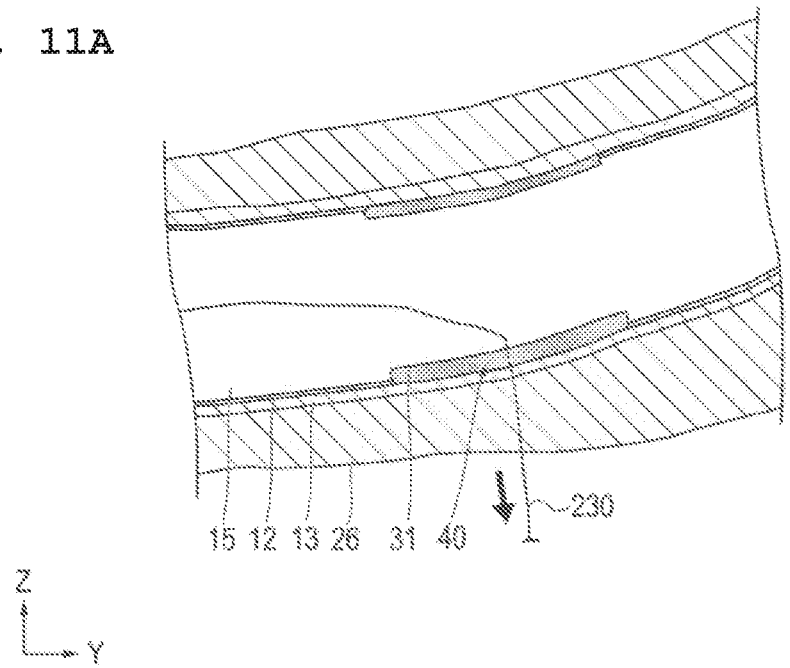
FIGS. 11A and 11B are sectional views for describing a use example and an operation of the medical device according to the second embodiment.
Figure 11B:
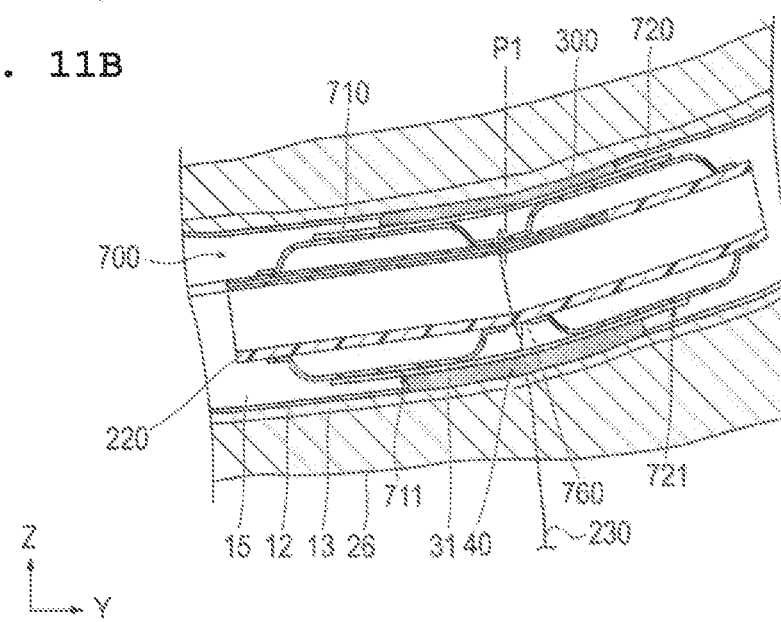

FIG. 10 is a view illustrating the medical device according to the second embodiment, and FIGS. 11A and 11B are views for describing a use example and an operation of the medical device according to the present embodiment.

As illustrated in FIG. 10, a medical device 700 according to the second embodiment has multiple balloons 710 and 720 disposed at different positions in the axial direction of the main body 220. Similarly, to the above-described balloon 210, the respective balloons 710 and 720 include effectively dilatable portions 711 and 721 on which the medical member 300 is mounted. The balloon 710 is referred to as a first balloon for convenience of description, and the balloon 720 is referred to as a second balloon for convenience of description.

The effectively dilatable portion 711 of the first balloon 710 and the effectively dilatable portion 721 of the second balloon 720 are arranged by leaving a mutually equal distance from the central position P1 of the main body 220. In this manner, the respective effectively dilatable portions 711 and 712 in the respective balloons 710 and 720 are respectively arranged at an axially symmetrical position with respect to the central position P1 of the main body 220.

The pressurizing medium flow path 228 formed in the main body 220 communicates with each of a dilating space 718 of the first balloon 710 and a dilating space 728 of the second balloon 720 so that a pressurizing medium can be supplied to the respective balloons 710 and 720. The respective balloons 710 and 720 are capable of dilating deformation and deflating deformation by operating the supply and discharge of the pressurizing medium via the tube 251 interlocked with the connector port 250.

An attachment portion 760 to which the guide member 230 can be attached is disposed between the first balloon 710 and the second balloon 720. The attachment portion 760 is formed of a step portion formed between the first balloon 710 and the second balloon 720 (gap partitioned by a step difference between the respective balloons 710 and 720 and the outer surface of the main body 220). In addition, the attachment portion 760 is formed in the vicinity of the central position P1 of the main body 220.

For example, as illustrated in FIG. 10, the guide member 230 can be attached to the main body 220 in such a way that the attachment portion 760 is annularly shaped along the circumferential direction of the step portion configuring the attachment portion 760 and the attachment portion 760 is caught on the outer surface of the main body 220. Since a specific member for attaching the guide member 230 is not used, the number of components can be reduced, and costs can be reduced. For example, in order to prevent the guide member 230 from being inadvertently detached in a state where the guide member 230 is attached to the main body 220, a configuration can be adopted in which the annually shaped state is maintained by performing fastening, bonding, welding, or the like on a portion of the guide member 230.

Next, a use example and an operation of the medical device 700 according to the present embodiment will be described. Hereinafter, an example of manual skills will be described in which the medical device 700 is delivered to the treatment site 40 formed by performing predetermined treatment on the scar tissue 31 formed in the bulbar urethra 15, and further in which the medical member 300 mounted on the medical device 700 is caused to indwell in the treatment site 40.

As illustrated in FIG. 11A, when the medical device 700 is used, the guide member 230 is first arranged at the treatment site 40 which is a treatment target site. In this case, the distal portion (end portion located on the distal side in the introducing direction) of the guide member 230 is extracted outward from the living body. For example, these treatments can be performed by using the rigid endoscope 500 and the puncture tool 400 as described above (refer to FIGS. 6A and 6B), and can be performed by using a predetermined puncture guide device 900 (to be described later) or the like (refer to FIG. 19).

Next, the proximal portion (end portion located on the proximal side in the introducing direction) of the guide member 230 is extracted outward from the living body via the bulbar urethra 15 (urethra 10) and the external urethral orifice 19. Then, as illustrated in FIG. 10, the guide member 230 is attached to the attachment portion 260 of the medical device 700 outside the living body.

Next, the medical device 700 is delivered to the treatment site 40 along the route T having the guide member 230 arranged therein, that is, the route T which connects the treatment site 40 formed in the bulbar urethra 15 and the outside of the living body to each other. For example, the medical device 700 is moved by pulling the distal portion of the guide member 230 outside the living body.

As illustrated in FIG. 11B, the main body 220 arranged in the bulbar urethra 15 is curved along an inner surface shape of the curved bulbar urethra 15. The effectively dilatable portion 711 of the first balloon 710 and the effectively dilatable portion 721 of the second balloon 720 are positioned at different positions in the extending direction (Y-axis direction) of the bulbar urethra 15.

After the respective balloons 710 and 720 of the medical device 700 are positioned at the treatment site 40, the respective balloons 710 and 720 are dilated and deformed. The medical member 300 is brought into contact with the treatment site 40 by dilating and deforming the respective balloons 710 and 720. In this case, the respective balloons 710 and 720 individually dilate and apply a pressurizing force to each portion of the bulbar urethra 15. Accordingly, the pressurizing force can be prevented from being unevenly applied in the extending direction of the curved bulbar urethra 15. In particular, in the medical device 700, the respective balloons 710 and 720 (respective effectively dilatable portions 711 and 721) can be arranged at the axially symmetrical position with respect to the central position P1 of the main body 220. Accordingly, the pressurizing force can be prevented from being unevenly applied in the extending direction of the treatment site 40.

As described above, according to the medical device 700 of the present embodiment, the multiple balloons 710 and 720 are disposed at the axially different positions of the main body 220. Accordingly, when the treatment site 40 falls within a predetermined range including the scar tissue 31 formed in the bulbar urethra 15 or the like, the pressurizing force can be prevented from being unevenly applied in the extending direction of the treatment site 40.

Next, a modification example of the above-described second embodiment will be described. In the description of the modification example, with regard to the same member as the previously described member or the element, which can be similarly configured, description thereof will be appropriately omitted.

Figure 12:
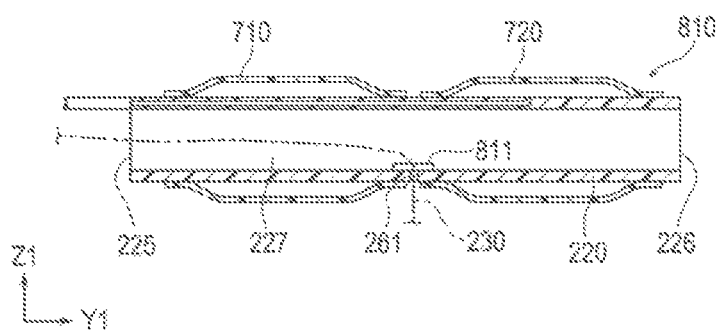
FIG. 12 is a partial sectional view illustrating a medical device according to Modification Example 1 of the second embodiment.

FIG. 12 illustrates a medical device 810 according to Modification Example 1 of the second embodiment.

In the medical device 810 according to Modification Example 1, an attachment portion for attaching the guide member 230 is configured to include a stopper 811 arranged inside (in the lumen 227) of the main body 220 and the hole portion 261 formed in the main body 220.

Figure 13A:
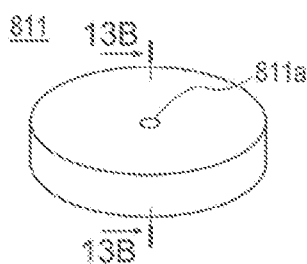
FIG. 13A is a perspective view of a stopper included in the medical device according to Modification Example 1 of the second embodiment.
Figure 13B:
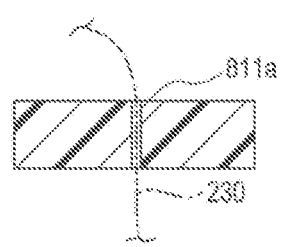
FIG. 13B is a sectional view taken along line 13B-13B illustrated in FIG. 13A.

As illustrated in FIGS. 13A and 13B, an insertion hole 811a penetrating the inside in the thickness direction is formed in the stopper 811. The guide member 230 is attached to the main body 220 by inserting the guide member 230 into the lumen 227 of the main body 220, the insertion hole 811a of the guide member 230, and the hole portion 261 of the main body 220. For example, the insertion hole 811a can be configured to have substantially the same inner diameter as the outer diameter of the guide member 230 so as to prevent the guide member 230 from being inadvertently moved, or can be configured to have the larger inner diameter than the outer diameter of the guide member 230 so as to enable the guide member 230 to be relatively easily moved.

For example, the stopper 811 can be configured by using a known elastic material or the like so that pressure applied when the guide member 230 is operated can be dispersed, and can be fixed to the main body 220 by means of welding, fusing, an adhesive, or the like. In addition, an outer shape of the stopper 811 is not limited to the illustrated elliptical shape, and can be appropriately changed.

Figure 14A:
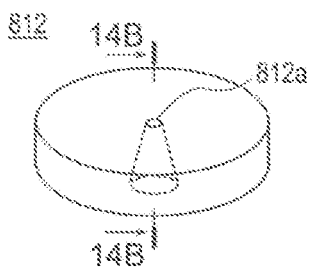
FIG. 14A is a perspective view of the stopper illustrating a modification example of the stopper included in the medical device according to Modification Example 1 of the second embodiment.
Figure 14B:
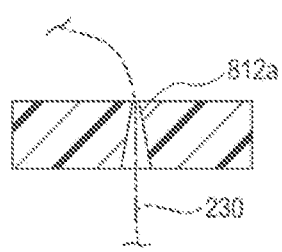
FIG. 14B is a sectional view taken along line 14B-14B illustrated in FIG. 14A.

FIGS. 14A and 14B illustrate a stopper 812 according to a modification example. An insertion hole 812a of the stopper 812 is formed in a tapered shape whose inner diameter gradually increases from the introduction side toward the extraction side (from the upper side toward the lower side in FIG. 14B) of the guide member 230. In the stopper 812 having this shape, the stopper 812 itself is deformed so as to follow a curved portion of the urethra 10. Accordingly, it is possible to prevent the curving performance of the medical device 200 from being degraded when the stopper 812 is used.

For example, without being configured to include the illustrated respective members 811 and 812, the stopper illustrated in Modification Example 1 can be configured to include a knot or the like of the guide member 230 which is formed so that the stopper can be caught on and engage with the hole portion 261 of the main body 220 or an upper surface of the hole portion 261. Alternatively, it is also possible to use those, which are configured to include a material other than an elastic material (for example, a hard resin material).

Figure 15A:
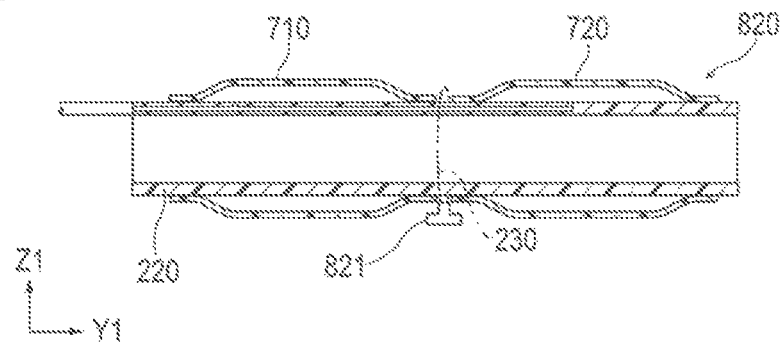
FIG. 15A is a view illustrating a medical device according to each modification example of the second embodiment, and which is a partial sectional view illustrating a medical device according to Modification Example 2.

FIG. 15A illustrates a medical device 820 according to Modification Example 2.

In the medical device 820 according to Modification Example 2, an attachment portion for attaching the guide member 230 is configured to include the stopper 821 arranged outside the main body 220 (outside the lumen 227) and the hole portion 261 formed in the main body 220. As illustrated in the present modification example, if the stopper 821 is arranged outside the main body 220, the guide member 230 can be attached outside the main body 220. Accordingly, it becomes possible to easily fix the annually shaped guide member 230.

A structure or the like of the stopper 821 is not particularly limited as long as the guide member 230 can be attached. For example, it is possible to use those which have a hole portion for fixing a portion of the guide member 230 by means of fitting or the like. In addition, the stopper 821 is arranged outside the main body 220. Accordingly, installation of the stopper 821 is less likely to affect the flexibility of the main body 220. For example, the stopper 821 can be configured to include a hard resin material.

Figure 15B:
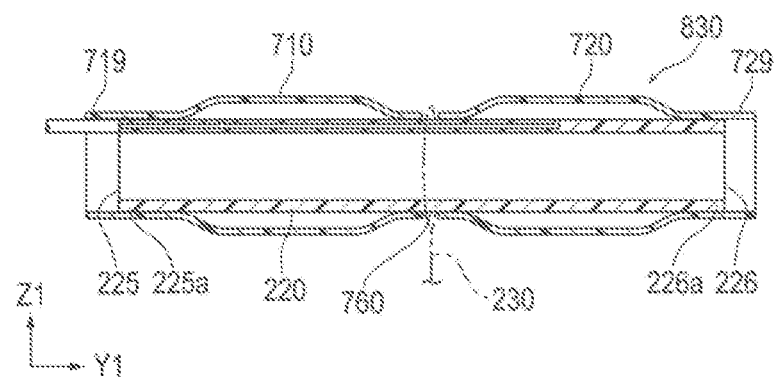
FIG. 15B is a partial sectional view illustrating a medical device according to Modification Example 3.

FIG. 15B illustrates a medical device 830 according to Modification Example 3 of the second embodiment.

In the medical device 830, the distal side end portion 226a of the main body 220 is covered with a distal side end portion 729 of the second balloon 720, and the proximal end portion 225a of the main body 220 is covered with a proximal side end portion 719 of the first balloon 710. According to this configuration, when the medical device 830 is introduced into the urethra 10, both end portions 225a and 226a of the main body can be prevented from rubbing against the inner wall of the urethra 10. Therefore, it is possible to realize less invasive manual skills.

Figure 15C:
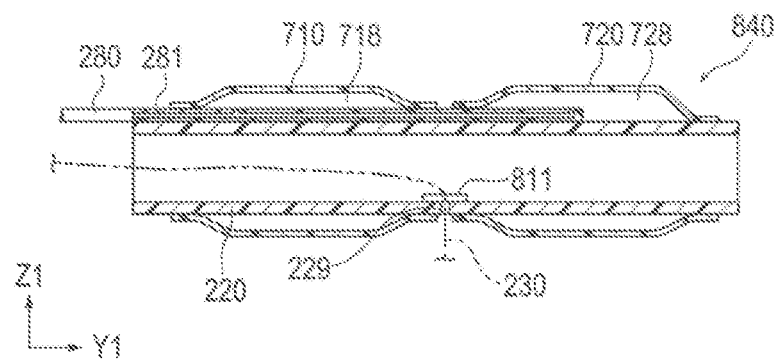
FIG. 15C is a partial sectional view illustrating a medical device according to Modification Example 4.

FIG. 15C illustrates a medical device 840 according to Modification Example 4 of the second embodiment.

In the medical device 840, the tube 280 which supplies the pressurizing medium to the respective balloons 710 and 720 is directly attached so as to face the inside of the respective dilating spaces 718 and 728. Even when the tube 280 is used, similarly to when the pressurizing medium supply flow path 228 formed inside the wall of the main body 220 is used as described above, the balloon 210 can be operated so as to be dilated and deflated by supplying and discharging the pressurizing medium via the flow path 281 of the tube 280.

Hereinafter, each modification example of a medical device will be described which is configured by adding the guide member 230 to the balloon device 120 configured to include the first balloon 710, the second balloon 720, the main body 220, and a film material 851.

Figure 16A:
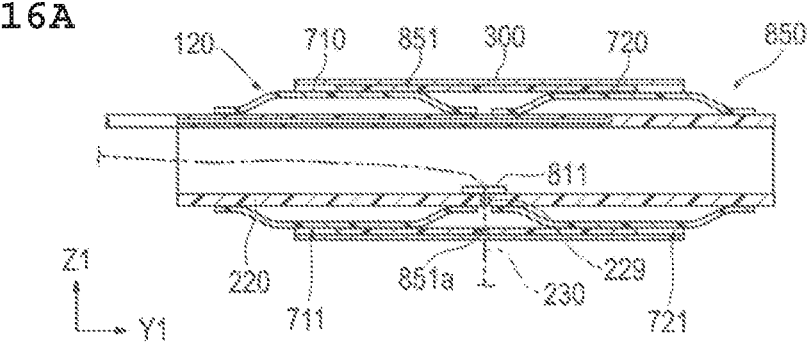
FIG. 16A is a view illustrating a medical device according to each modification example of the second embodiment, which illustrates a partial sectional view illustrating a medical device according to Modification Example 5.

FIG. 16A illustrates a medical device 850 according to Modification Example 5 of the second embodiment.

In the medical device 850, the flexible film material 851 arranged so as to cover each outer surface of the respective balloons 710 and 720 is provided.

The film material 851 is formed in a hollow cylindrical shape, and is mounted on the outer surface of the respective balloon 710 and 720 by inserting the respective balloon 710 and 720 into the film material 851. For example, the film material 851 can be configured to include the same flexible material as the configuration material of the above-described balloon 210. In addition, the thickness, the axial length, the outer diameter, or the like of the film material 851 can be appropriately changed as long as the curving performance (deformable performance with respect to the urethral inner wall) of the main body 220 is not degraded.

A hole portion 851a for extracting the guide member 230 outward from the respective balloons 710 and 720 is disposed in the film material 851.

The film material 851 included in the medical device 850 helps prevent a step difference present between the respective balloons 710 and 720 from being exposed outward. Therefore, when the medical device 850 is used, it is possible to reduce possibilities that a load may be applied to the inner wall of the urethra 10 or sliding resistance may increase during the introduction of the medical device 850 since the step difference between the respective balloons 710 and 720 is brought into contact with or caught on the inner wall of the urethra 10. In addition, the medical member 300 is arranged on the outer surface of the smooth film material 851. Accordingly, the medical member 300 can be prevented from being wrinkled or bent. Therefore, a treatment effect of the medical member 300 can be improved.

Figure 16B:
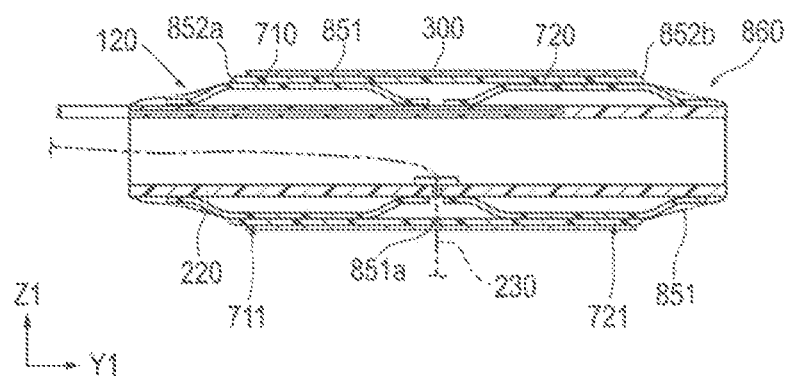
FIG. 16B is a partial sectional view illustrating a medical device according to Modification Example 6.

FIG. 16B illustrates a medical device 860 according to Modification Example 6 of the second embodiment.

The film material 851 included in the medical device 860 can be formed in a shape which is curved so that both end portions 852a and 852b in the axial direction are rounded. According to this configuration, it is possible to reduce sliding resistance of the medical device 860 inside the urethra 10. In addition, for example, the length (dimension in the axial direction) of the film material 851 can be formed to be the length, which covers the overall effectively dilatable portions 711 and 721 of the respective balloons 710 and 720 as illustrated in the present modification example.

In addition, for example, the film material 851 can be configured to have the length which can cover the distal portion of the first balloon 710 and the proximal portion of the second balloon 720 as illustrated by a two-dot chain line in the drawing. Furthermore, the film material 851 can also be configured to have a shape whose diameter decreases toward each of the distal side and the proximal side so that the inner diameter of both end portions in the axial direction of the film material 851 is approximately equal to the outer diameter of the main body 220. According to this configuration, the film material 851 can be fixed to the main body 220 and the respective balloons 710 and 720 via both end portions of the film material 851. Accordingly, it is possible to omit fixing work using an adhesive, or by means of welding or the like.

Figure 16C:
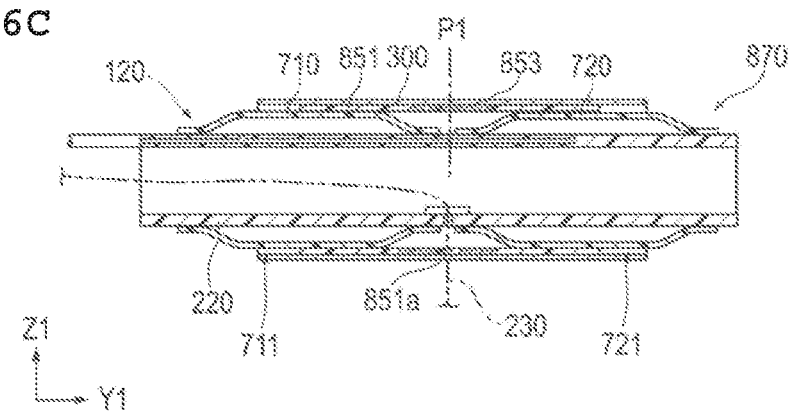
FIG. 16C is a partial sectional view illustrating a medical device according to Modification Example 7.

FIG. 16C illustrates a medical device 870 according to Modification Example 7 of the second embodiment.

An easily deformable portion 853 which can be more easily curved than the other portions in the film material 851 is formed in the film material 851 included in the medical device 870.

The easily deformable portion 853 is configured to include a slit formed in the film material 851. A portion having the slit formed in the film material 851 is formed to be thinner than the other portions. Accordingly, the portion is likely to be curved and deformed. In addition, as illustrated, the easily deformable portion 853 is formed in the vicinity of the central position P1 of the main body 220, that is, in the vicinity of an intermediate position between the respective balloons 710 and 720. Therefore, when the medical device 870 is used, the film material 851 is deformed to follow a shape of the curved or meandering inner wall in the urethra 10 from the easily deformable portion 853 serving as the starting point. Therefore, when the respective balloons 710 and 720 are dilated, the pressurizing force can be prevented from being unevenly applied to the treatment site 40.

For example, the easily deformable portion 853 can also be configured by adding a bellows structure to the film material 851 or by adding an extendable bent portion to the film material 851. In addition, the easily deformable portion 853 can also be disposed in the vicinity of the central position P1 of the main body 220 and/or in the portion other than the central position P1. Alternatively, the easily deformable portion 853 can also be disposed at multiple different locations in one film material 851.

Figure 17B:
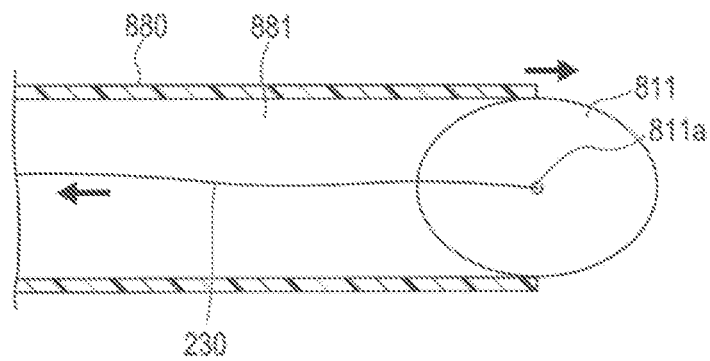
FIG. 17B is an arrow view when viewed in a direction of an arrow 17B in FIG. 17A.

FIGS. 17A and 17B illustrate a work example when the above-described medical device 850 (refer to FIG. 16A) is introduced into the urethra 10.

For example, when the medical device 850 is delivered to the treatment site 40, a known guiding catheter 880 can be used.

When the guiding catheter 880 is used, as illustrated in FIGS. 17A and 17B, the guide member 230 attached to the medical device 850 is first inserted into a lumen 881 of the guiding catheter 880, and the guiding catheter 880 is moved along the guide member 230. In addition, in this case, while the guide member 230 is pulled outside the living body by the hand operation, the stopper 811 is pushed in the distal portion of the guiding catheter 880. In this manner, the medical device 850 can be smoothly moved inside the urethra 10. This introduction method is similarly applicable to the medical devices 860 and 870 (refer to FIGS. 16A and 16B) in which the stopper 811 is arranged inside the main body 220.

According to the balloon device 120 in each of Modification Examples 5 to 7 of the second embodiment, a balloon device can be provided, which has the multiple balloons 710 and 720, the main body 220, and the film material 851, and which can easily extract the guide member 230 inserted into the lumen 227 of the main body 220 to the outer surface side of the film material 851.

Next, a puncture guide device 900 will be described with reference to FIGS. 18A, 18B, and 19.

For example, the puncture guide device 900 can be used in order to confirm a puncture position for the treatment site 40 before the respective medical devices 700, 810, 820, 830, 840, 850, 860, and 870 according to the second embodiment which include the multiple balloons 710 and 720 are positioned and arranged in the curved portion like the bulbar urethra 15. The puncture guide device 900 configures a predetermined medical device in combination with the respective medical devices 700, 810, 820, 830, 840, 850, 860, and 870 or the medical device assembly (combination between the medical device and the puncture tool 400).

Figure 18A:
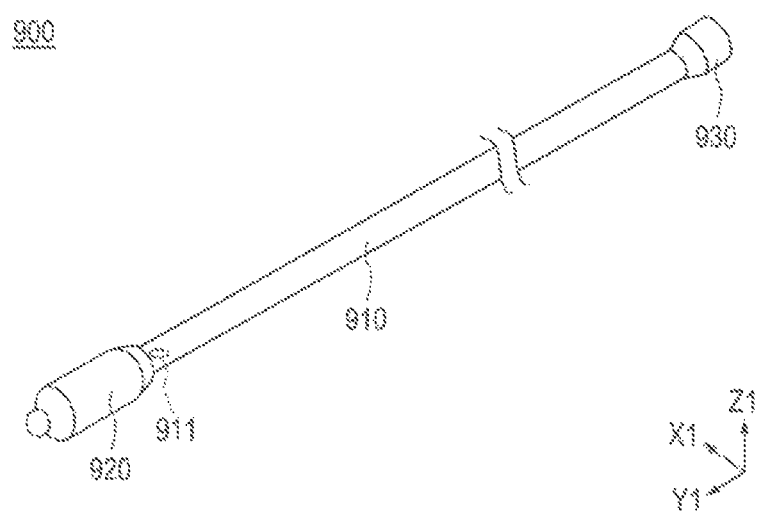
FIG. 18A is a view illustrating a puncture guide device according to an embodiment, and which illustrates a perspective view of the puncture guide device.
Figure 18B:
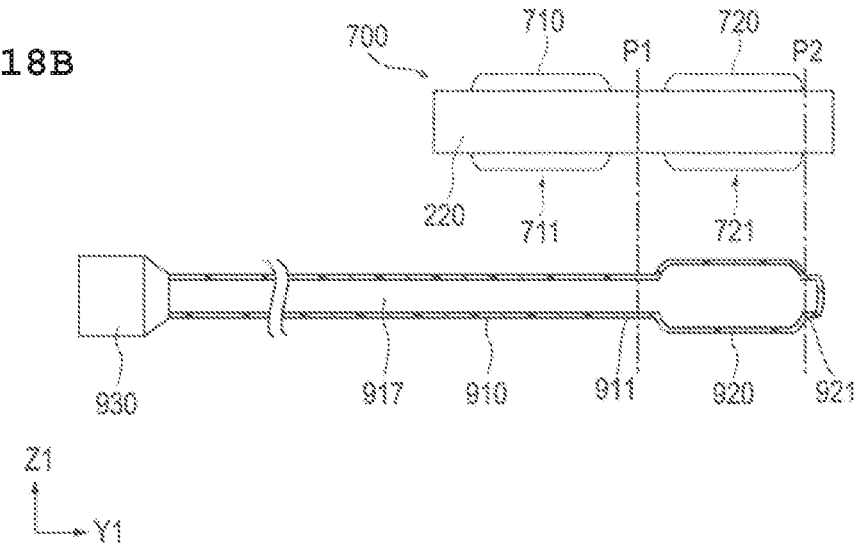
FIG. 18B is a partial sectional view of the puncture guide device.

As illustrated in FIGS. 18A and 18B, the puncture guide device 900 has a flexible and elongated main body 910, a distal guide portion 920 arranged in the distal portion of the main body 910, and a hub 930 arranged in the proximal portion of the main body 910.

Figure 19:
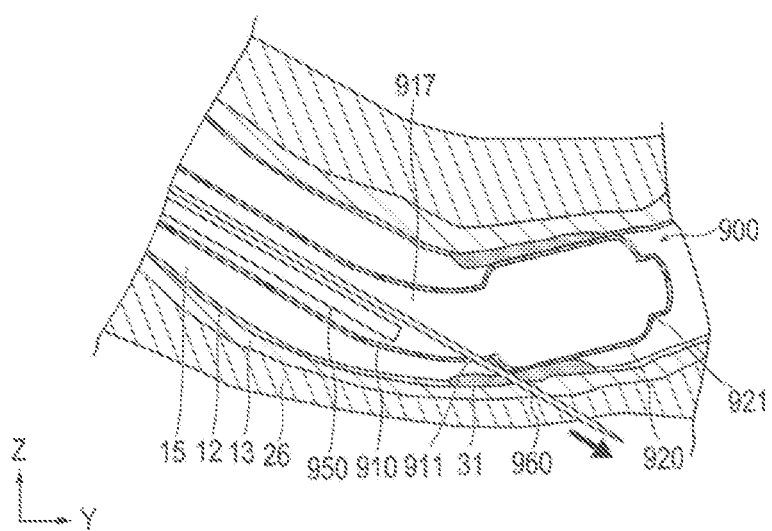
FIG. 19 is a sectional view illustrating a use example of the puncture guide device.

The main body 910 and the hub 930 of the puncture guide device 900 are configured to be capable of inserting and penetrating a medical tool such as a known rigid endoscope 950, a puncture tool 960 having a puncture needle and the like (refer to FIG. 19). For example, the main body 910 of the puncture guide device 900 can be configured to include the same material as that of the main body 220 of the medical device 200.

The distal guide portion 920 is configured to include a flexible material, and is formed in a shape in which the outer shape imitates the second balloon 720 as illustrated in FIG. 18B. In addition, the distal guide portion 920 is shaped in the production stage so as to maintain the outer shape before and after the distal guide portion 920 is introduced into the urethra 10. For example, a configuration material of the distal guide portion 920 can be configured to include the same material as that of the above-described balloon 210.

The main body 910 and the distal guide portion 920 can be formed to be transparent or semi-transparent so that the outside is visible from the inside of the main body 910 and the distal guide portion 920. In addition, a convex portion curved to the distal side is disposed in the most distal end portion of the distal guide portion 920. The convex portion has a function to guide the movement of the distal guide portion 920 when the distal guide portion 920 is moved inside the urethra 10, and a function to prevent damage to the urethra 10 or the like when the distal guide portion 920 abuts against the inner wall of the urethra 10.

The main body 910 has a lumen 917 which extends in the axial direction and a guide hole 911 for allowing the puncture tool 960 (refer to FIG. 19) to penetrate through the inside and the outside of the main body 910. As illustrated in FIG. 18B, the guide hole 911 is formed away from a distal end 921 of the distal guide portion 920 to the proximal side by a predetermined distance. The distance is set so as to coincide with a distance between the distal portion of the second balloon 720 and the central position P1 of the main body 220 in the medical device 700.

Next, a use example of the puncture guide device 900 will be described.

As illustrated in FIG. 19, before the medical device 700 is used, the puncture guide device 900 is introduced into the bulbar urethra 15. The distal guide portion 920 is positioned and arranged at the treatment site 40, which is a treatment target site. The puncture guide device 900 can be delivered and positioned by using the puncture guide device 900 together with the predetermined rigid endoscope 950.

After the distal guide portion 920 is positioned, the predetermined puncture tool 960 punctures a puncture target position. In this case, the puncture tool 960 is caused to protrude from the guide hole 911 of the main body 910. As described above, the distance between the guide hole 911 and the distal end 921 of the distal guide portion 920 is set so as to coincide with the distance between the distal portion of the second balloon 720 and the central position P1 of the main body 220 in the medical device 700. Therefore, while the position of the distal guide portion 920 is confirmed, the puncture is performed via the guide hole 911 by the puncture tool 960. In this manner, a position relationship can be confirmed between the second balloon 720 of the medical device 700 to be introduced after the puncture and the central position P1 (position of the attachment portion 760) of the main body 220. Therefore, when the puncture work is carried out, a relative position relationship can be recognized between the treatment site 40 and the medical device 700. Accordingly, the medical device 700 can be positioned at a more suitable position.

For example, the distal guide portion 920 can also be configured to include a member capable of dilating deformation and deflating deformation such as the balloon. When the distal guide portion 920 is configured to include the balloon, as the pressurizing medium for dilation, it is possible to use a liquid (perfusion liquid or the like) supplied from a channel or the like of the rigid endoscope 950, for example. In addition, a configuration of the puncture guide device 900 can be changed so that the work for positioning or the like of the puncture position can be carried out by disposing a visible marker or the like (colored portion or a predetermined member) instead of the guide hole 911.

Hitherto, the medical device and the medical device assembly according to the present disclosure have been described with reference to the multiple embodiments and modification examples. However, without being limited only to the configurations described in the embodiments, the present disclosure can be appropriately modified based on the disclosure in Claims.

For example, the medical device and the medical device assembly according to the present disclosure are also applicable to any site inside the urethra (for example, a site on the external urethral orifice or a site on the prostate), and are also applicable to another use in addition to the treatment for preventing the urethral stricture from recurring. In addition, the medical device and the medical device assembly according to the present disclosure can be used in order to cause a predetermined medical member to indwell in other biological organs in addition to the urethra (for example, urethra, blood vessel, esophagus, airway, bowel, pancreatic duct, bile duct, ear, nasal cavity, paranasal sinus, and the like). A shape, a structure, a function, or the like of the medical member is not particularly limited as long as the medical member is used, for example, in order to recover or improve a function of the treatment target site and in order to treat a disease. The medical member may be another one in addition to the sheet-like one, which provides the epithelial function.

In addition, the respective configurations described in each embodiment and each modification example can be adopted in combination with the medical device and the medical device assembly according to another embodiment or another modification example as long as the functions are not impaired.

The detailed description above describes a medical device used in delivering a medical member, a medical device assembly including the medical device, a balloon device, and a treatment method for treating a urethral stricture. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical system comprising:
a medical device and a medical member, the medical device configured to deliver the medical member, the medical device comprising:
   a flexible main body that extends in an axial direction;
   a balloon that includes a dilatable portion on which the medical member is mounted, the balloon having a dilating space into which a pressurizing medium flows between an outer surface of the flexible main body and an inner surface of the balloon;
   an elongated guide member configured to extend across the treatment target site and outside of a living body via the biological lumen;
   an attachment portion to which at least a portion of the guide member is detachably attached to the flexible main body at a position between end portions of the flexible main body in the axial direction;
   the flexible main body being configured to be movable inside the biological lumen along a route having the elongated guide member arranged in the flexible main body, in a state where the guide member is attached to the attachment portion, the flexible main body having a lumen which extends in the axial direction, an opening portion for inserting the guide member into the lumen, and a hole portion configured to guide the guide member from the lumen to an outside of the flexible main body, and an extracting portion configured to guide the guide member from the hole portion to an outer surface side of the balloon, the extracting portion having a through-hole disposed in the balloon, and wherein a portion of an outer surface of the balloon around the through-hole is fixed to a periphery of the hole portion of the flexible main body; and
wherein the medical member is a sheet shaped member configured to provide a biological tissue with an epithelial function, and wherein the sheet shaped member is configured to be introduced into the biological lumen in a state where the sheet shaped member is wound around the dilatable portion of the balloon, and a gap in the sheet shaped member through which the guide member can be inserted in a state in which the sheet shaped member is wrapped around the dilatable portion of the balloon in a circumferential direction; and a puncture tool including a main body having a lumen configured to receive the guide member and a puncture needle to which the guide member is attached so as to be connectable to the puncture needle and detachable from the puncture needle.

2. The medical system according to claim 1,
wherein the extracting portion is configured to include the through-hole disposed in a thermally welded portion of the balloon formed by thermally welding the portion of the balloon to the periphery of the hole portion of the flexible main body.

3. The medical system according to claim 1,
wherein the attachment portion is disposed in a central position in the axial direction of the flexible main body; and
wherein the dilatable portion of the balloon has a symmetrically dilated shape at the central position in the axial direction of the flexible main body.

4. The medical system according to claim 1, comprising:
a stopper configured to be disposed inside the flexible main body and/or outside the flexible main body and configured to restrict mobility of the guide member.

5. The medical system according to claim 1, wherein the puncture tool further comprises:
a hub having a lock mechanism configured to switch between fixing and unfixing of the guide member.

6. The medical system according to claim 1, wherein the medical device is configured to deliver the medical member to a urethral stricture.

7. The medical system according to claim 1, wherein the sheet shaped member has a cylindrical shape upon dilation of the dilating portion of the balloon in a treatment target site.

8. The medical system according to claim 1, wherein the sheet shaped member includes an agent, gel, micro beads, and a synthetic polymer configured to promote regeneration of an epithelial function, or a material serving to replace recovery of the epithelial function; and
a suture thread configured to fix the sheet shaped member into a cylindrical shape in the state where the sheet shaped member is wound around the dilatable portion of the balloon.

9. A medical system comprising:
a balloon device, the balloon device including a flexible main body that extends in an axial direction, the flexible main body has a lumen which extends in the axial direction, an opening portion for inserting an elongated guide member into the lumen, and a hole portion which extracts the guide member from the lumen to outside of the flexible main body, and an extracting portion configured to guide the guide member from the hole portion to an outer surface side of the balloon, the extracting portion having a through-hole disposed in the balloon, and wherein a portion of an outer surface of the balloon around the through-hole is fixed to a periphery of the hole portion of the flexible main body;
a balloon having a dilatable portion on which a medical member is attached, the balloon having a dilating space into which a pressurizing medium flows between an outer surface of the flexible main body and an inner surface of the balloon, the medical member being a rectangular shaped sheet wound around an outer surface of the balloon in a circumferential direction before a dilation of the balloon, and a gap in the medical member through which the guide member can be inserted in a state in which the medical member is wrapped around the dilatable portion of the balloon in the circumferential direction;
wherein the balloon includes an extracting portion configured to guide the guide member from the hole portion to an outer surface side of the balloon; and
a puncture tool including a main body having a lumen configured to receive the guide member and a puncture needle to which the guide member is attached so as to be connectable to the puncture needle and detachable from the puncture needle.

10. The medical system according to claim 9,
wherein the extracting portion is configured to include the through-hole disposed in a thermally welded portion of the balloon formed by thermally welding the portion of the balloon to the periphery of the hole portion of the main body.

11. The medical system according to claim 9,
wherein the attachment portion is disposed in a central position in the axial direction of the flexible main body; and
wherein the dilatable portion of the balloon has a symmetrically dilated shape at the central position in the axial direction of the flexible main body.

12. The medical system according to claim 9, wherein the medical member has a cylindrical shape upon dilation of the dilating portion of the balloon in a treatment target site.

13. The medical system according to claim 9, wherein the medical member includes an agent, gel, micro beads, and a synthetic polymer configured to promote regeneration of an epithelial function, or a material serving to replace recovery of the epithelial function; and
a suture thread configured to fix the medical member into a cylindrical shape in the state where the medical member is wound around the dilatable portion of the balloon.

14. A treatment method for a urethral stricture comprising:
forming a treatment site by performing predetermined treatment on a scar tissue formed in a urethra;
arranging an elongated guide member at the treatment site via the urethra;
delivering a medical device including a balloon having a medical member mounted on the balloon to the treatment site along the guide member, the medical device including a flexible main body that extends in an axial direction, the balloon having a dilating space into which a pressurizing medium flows between an outer surface of the flexible main body and an inner surface of the balloon, the elongated guide member configured to extend across the treatment target site and outside of a living body via the biological lumen, an attachment portion to which at least a portion of the guide member is detachably attached to the flexible main body at a position between end portions of the flexible main body in the axial direction, the flexible main body being configured to be movable inside the biological lumen along a route having the elongated guide member arranged in the flexible main body, in a state where the guide member is attached to the attachment portion, and wherein the medical member is a sheet shaped member configured to provide a biological tissue with an epithelial function, and wherein the sheet shaped member is configured to be introduced into the biological lumen in a state where the sheet shaped member is wound around the dilatable portion of the balloon, and a gap in the sheet shaped member through which the guide member can be inserted in a state in which the sheet shaped member is wrapped around the dilatable portion of the balloon in a circumferential direction; attaching the guide member to a puncture tool, the puncture tool including a main body having a lumen configured to receive the guide member and a puncture needle to which the guide member is attached so as to be connectable to the puncture needle and detachable from the puncture needle; and causing the medical member to indwell over a predetermined period of time by dilating the balloon positioned at the treatment site and maintaining a state where the medical member is brought into contact with the treatment site.

15. The treatment method for a urethral stricture according to claim 14, comprising:

inserting the guide member into the outside of the urethra from the inside of the urethra.

16. The treatment method for a urethral stricture according to claim 15, comprising:

connecting the guide member and a stopper to each other outside the urethra.

\* \* \* \* \*